United States Patent
Gruza et al.

(10) Patent No.: US 9,073,813 B2
(45) Date of Patent: Jul. 7, 2015

(54) PROCESS FOR THE PREPARATION OF PROTOESCIGENIN

(71) Applicants: INSTYTUT FARMACEUTYCZNY, Warsaw (PL); WARSZAWSKI UNIWERSYTET MEDYCZNY, Warsaw (PL)

(72) Inventors: Mariusz Gruza, Warsaw (PL); Oliwia Zegrocka-Stendel, Lomianki (PL); Tomasz Giller, Lodz (PL); Grzegorz Grynkiewicz, Lomianki (PL); Marta Laszcz, Warsaw (PL); Kamil Jatczak, Plock (PL)

(73) Assignees: INSTYTUT FARMACEUTYCZNY, Warsaw (PL); WARSZAWSKI UNIWERSYTET MEDYCZNY, Warsaw (PL)

( * ) Notice: Subject to any disclaimer, the term of this patent is extended or adjusted under 35 U.S.C. 154(b) by 11 days.

(21) Appl. No.: 13/733,855

(22) Filed: Jan. 3, 2013

(65) Prior Publication Data
US 2013/0190538 A1 Jul. 25, 2013

Related U.S. Application Data

(63) Continuation-in-part of application No. PCT/PL2012/000102, filed on Oct. 12, 2012.

(30) Foreign Application Priority Data

Oct. 12, 2011 (PL) ........................................ 396618

(51) Int. Cl.
C07C 29/09 (2006.01)
C07C 35/44 (2006.01)
(Continued)

(52) U.S. Cl.
CPC .............. *C07C 29/095* (2013.01); *C07C 29/74* (2013.01); *C07C 29/78* (2013.01); *C07C 31/278* (2013.01); *C07J 63/00* (2013.01); *C07C 35/44* (2013.01)

(58) Field of Classification Search
CPC ...... C07C 29/095; C07C 35/44; C07C 29/74; C07C 29/78; C07C 29/10
USPC ......... 568/817, 822, 823, 832, 858, 877, 868, 568/913; 560/220
See application file for complete search history.

(56) References Cited

U.S. PATENT DOCUMENTS

2012/0277308 A1* 11/2012 Chan et al. ................... 514/533

OTHER PUBLICATIONS

Chen et al. "Studies on the Constituents of Xanthoceras sorbifolia Bunge. IV. Structures of the Minor Prosapogenins" Chem. Pharm. Bull. 1985, v33, pp. 1043-1048.*

(Continued)

*Primary Examiner* — Jafar Parsa
*Assistant Examiner* — Medhanit Bahta
(74) *Attorney, Agent, or Firm* — Matthias Scholl, PC; Matthias Scholl

(57) ABSTRACT

A process for the preparation of protoescigenin by hydrolysis of escin isolated from *Aesculus hippocastanum*. The process includes the following steps: a two-step hydrolysis first under acidic and then basic conditions, enrichment of the crude mixture of sapogenins with protoescigenin, an isolation of the mixture of sapogenins in a solid form, and a purification of the obtained solid and isolation of high purity protoescigenin. The invention also relates to protoescigenin monohydrate in a crystalline form and the preparation thereof. Protoescigenin is a polyhydroxy aglycone, which can be used as a synthon in the chemical modifications of naturally occurring saponins.

23 Claims, 13 Drawing Sheets

(51) Int. Cl.
*C07C 29/74* (2006.01)
*C07C 29/78* (2006.01)
*C07C 29/10* (2006.01)
*C07C 31/27* (2006.01)
*C07J 63/00* (2006.01)

(56) References Cited

OTHER PUBLICATIONS

Yosioka et al. "On Genuine Sapogenins of Horse Chestnut Saponins by means of Soil Bacterial Hydrolysis and a new minor Sapogenin: 16-Desoxy-Barringtogenol C" Tetrahedron Lett. 1967, v27, pp. 2577-2580; and J. Nat. Products 1991, v54, pp. 1394-1396.*

Agrawal et al. "Application of 2D NMR Spectroscopy to the Structural Establishment of the Major Hydrolysis Product of Aescin" J. Nat. Products 1991, v54, pp. 1394-1396.*

Gruza et al. "Preparation of protoaescigenin from escin" VIII Multidyscyplinarna Konferencja Nauki o Leku, Mar. 6, 2012.*

I. Yosioka, et al, Saponin and Sapogenol. IV. Seeds Sapogenols of *Aesculus turbinata* BLUME. On the Configuration of Hydroxyl Functions in Ring E of Aescigenin, Protoaescigenin, and Isoaescigeninin Relation to Barringtogenol C and Theasapogenol A, Chem. Pharm. Bull., 1971, pp. 1200-1213, vol. 19, No. 6, The Pharmaceutical Society of Japan, Tokyo, Japan.

M. Yoshikawa, et al, Escins-Ia, Ib, IIa, IIb, and IIIa, Bioactive Triterpene Oligoglycosides from the Seeds of *Aesculus hippocastanum* L.: Their Inhibitory Effects on Ethanol Absorption and Hypoglycemic Activity on Glucose Tolerance Test, Chem. Pharm. Bull., 1994, pp. 1357-1359, vol. 42, No. 6, The Pharmaceutical Society of Japan, Tokyo, Japan.

M. Yoshikawa, et al, Bioactive Saponins and Glycosides. III. Horse Chestnut. (1): The Structures, Inhibitory Effects on Ethanol Absorption, and Hypoglycemic Activity of Escins Ia, Ib, IIa, IIb, and IIIa from the Seeds of *Aesculus hippocastanum* L., Chem. Pharm. Bull., 1996, pp. 1454-1464, vol. 44, No. 8, The Pharmaceutical Society of Japan, Tokyo, Japan.

M. Yoshikawa, et al, Bioactive Saponins and Glycosides. XII. Horse Chestnut. (2): Structures of Escins IIIb, IV, V, and VI and Isoescins Ia, Ib, and V, Acylated Polyhydroxyoleanene Triterpene Oligoglycosides, from the Seeds of Horse Chestnut Tree (*Aesculus hippocastanum* L., Hippocastanaceae), Chem. Pharm. Bull., 1998, pp. 1764-1769, vol. 46, No. 11, The Pharmaceutical Society of Japan, Tokyo, Japan.

H. Matsuda, et al, Effects of Escins Ia, Ib, and IIb from Horse Chestnut, the Seeds of *Aesculus hippocastanum* L., on Acute Inflammation in Animals, Biol. Pharm. Bull. 1997, pp. 1092-1095, vol. 20, No. 10, The Pharmaceutical Society of Japan, Tokyo, Japan.

Z. Zhang, et al, An overview of genus *Aesculus* L.: ethnobotany, phytochemistry, and pharmacological Activities. Pharmaceutical Crops., 2010, pp. 24-51, vol. 1, Bentham Science Publishers, Sharjah, United Arab Emirates.

* cited by examiner

Table 1

| Series (Product) | Substrate | weight [g] | yield [%] | Solvent 1 | V1 [ml] | Solvent 2 | V2 [ml] | Temp. / conditions | RRT 0.95 | PES-01 1.00 | 1.06 | 1.09 | BAC-01 1.14 | Others RRT. peak area |
|---|---|---|---|---|---|---|---|---|---|---|---|---|---|---|
| *1.0* | | | | | | | | | | | | | | |
| 1.1-1 | 1.0 | 3.65 | 59.8 | MeOH | 200 | - | - | Reflux | *2.84* | 73.83 | *0.81* | *3.00* | *3.66* | *1.47 (1.43); 1.53 (2.79); 2.17 (11.65)* |
| 1.2-1 | 1.1-1 | 1.97 | 55.3 | MeOH | 85 | - | - | Reflux; distillation | 3.23 | 78.51 | 0.84 | 0.62 | 1.11 | 1.47 (1.59); 1.53 (2.96); 2.17 (11.77) |
| 1.3-1 | 1.2-1 | 1.43 | 75.3 | MeOH | 40 | - | 40 | Reflux | 4.28 | 90.39 | 0.84 | 0.55 | 0.39 | 2.17 (3.54) |
| 1.4-1 | 1.3-1 | 0.75 | 62.4 | MeOH | 130 | - | - | Reflux | 5.28 | 92.65 | 1.02 | 0.83 | 0.21 | |
| | | | | | | | | | 5.07 | 93.20 | 0.92 | 0.74 | 0.07 | |
| *5.0* | | | | | | | | | *3.03* | *87.16* | *0.63* | *2.67* | *5.29* | |
| 5-31 | 5.0 | 0.27 | 52.89 | MeOH | 13 | - | - | Reflux | 3.30 | 93.41 | 0.71 | 0.92 | 1.67 | |
| 5-32 | 5.0 | 0.35 | 69.20 | MeOH | 14 | - | 7 | Reflux. distillation | 3.44 | 91.24 | 0.74 | 1.11 | 2.69 | |
| 5-33 | 5.0 | 0.23 | 45.80 | MeOH | 6.5 | - | - | Maceration at reflux | 2.86 | 90.25 | 0.62 | 1.05 | 4.36 | |

FIG. 7

Table 2

| Series (Product) | Substrate | eight [g] | Yield [%] | Solvent 1 | V1 [ml] | Solvent 2 | V2 [ml] | RRT 0.95 | PES-01 1.00 | 1.06 | 1.09 | BAC-01 1.14 | Others RRT, peak area |
|---|---|---|---|---|---|---|---|---|---|---|---|---|---|
| 3.1 | 3.0 | 3.52 | 60.6 | MeOH | 100 | CH₃CN | 100 | 3.09 | 78.72 | 0.60 | 0.17 | 1.36 | 1.47 (1.63); 1.53 (3.09); 2.17 (8.50) |
| 3.2-2 | 3.1 | 0.09 | 17.6 | MeOH | 10 | EtOH | 9.5 | 4.86 | 93.43 | 0.56 | 0.27 | 0.45 | |
| 3.2-3 | 3.1 | 0.19 | 37.6 | MeOH | 10 | Ipoh | 8.5 | 4.81 | 93.81 | 0.61 | 0.29 | 0.47 | |
| 3.2-4 | 3.1 | 0.23 | 46.2 | EtOH | 20 | Tol/Hex | 25+50 | 5.17 | 94.37 | 0.22 | 0.10 | 0.09 | |
| 3.2-5 | 3.1 | 0.05 | 10.0 | iPrOH | 5 | - | - | 4.05 | 94.22 | 0.47 | 0.24 | 0.88 | |
| 2.1 | 2.0 | 2.80 | 54.6 | MeOH | 130 | - | - | 2.60 | 94.12 | 0.56 | 0.28 | 1.77 | |
| 2.2-5 | 2.1 | 0.12 | 25.3 | Acetone | 76 | - | - | 4.29 | 94.70 | 0.45 | 0.07 | 0.21 | |
| 3.0 | | | | | | | | 2.48 | 75.78 | 0.62 | 1.52 | 5.07 | 1.47 (1.38); 1.53 (2.68); 2.17 (10.98) |
| 3.1 | 3.0 | 3.52 | 60.6 | MeOH | 100 | CH₃CN | 100 | 3.09 | 78.72 | 0.60 | 0.17 | 1.36 | 1.47 (1.63); 1.53 (3.09); 2.17 (8.50) |

FIG. 8a

Table 2 (continued)

| Series (Product) | Substrate | weight [g] | Yield [%] | solvent 1 | V1 [ml] | Solvent 2 | V2 [ml] | RRT | PES-01 | | | BAC-01 | Others RRT, peak area |
|---|---|---|---|---|---|---|---|---|---|---|---|---|---|
| | | | | | | | | *0.95* | *1.00* | *1.06* | *1.09* | *1.14* | |
| 4.0 | | | | | | | | | | | | | |
| 4.1-2 | 4.0 | 0.26 | 51.6 | MeOH | 13 | iPr₂O | 5 | 3.32 | 91.60 | 1.06 | 1.18 | 2.50 | |
| 4.1-3 | 4.0 | 0.23 | 48.2 | MeOH | 14 | THF | 2.5 | 4.25 | 92.83 | 1.01 | 1.12 | 0.78 | |
| | | | | | | | | 4.03 | 92.22 | 1.17 | 1.47 | 1.12 | |
| 5.0 | | | | | | | | | | | | | |
| 5-34 | 5.0 | 0.36 | 72.80 | EtOH | 3.8 | Hex | 16 | 3.03 | 87.16 | 0.63 | 2.67 | 5.29 | |
| 5-35 | 5.0 | 0.41 | 83.40 | EtOH | 4.2 | CyH | 25 | 3.59 | 92.78 | 0.40 | 1.37 | 0.98 | |
| 5-36 | 5.0 | 0.37 | 75.00 | EtOH | 4 | Hep | 7 (+3)* | 3.47 | 91.59 | 0.60 | 1.79 | 1.14 | |
| 5-37 | 5.0 | 0.32 | 63.20 | iPrOH | 7.5 | Hex | 35 | 3.61 | 92.13 | 0.48 | 2.05 | 1.14 | |
| 5-38 | 5.0 | 0.10 | 48.50 | iPrOH | 2.5 | CyH | 5 | 3.20 | 91.37 | 0.44 | 1.35 | 2.52 | |
| 5-39 | 5.0 | 0.39 | 77.60 | iPrOH | 5 | CyH | 25 (+12)* | 4.21 | 90.34 | 0.63 | 2.31 | 1.33 | |
| 5-40 | 5.0 | 0.11 | 54.00 | iPrOH | 2.5 | Hep | 10 | 3.39 | 91.06 | 0.57 | 2.38 | 1.17 | |
| 5-41 | 5.0 | 0.30 | 60.20 | iPrOH | 7 | Hep | 15 (+7)* | 3.24 | 91.67 | 0.40 | 1.35 | 2.53 | |
| | | | | | | | | 3.64 | 91.26 | 0.47 | 1.93 | 1.03 | |

\* added after solid precipitation; MeOH -- methanol; EtOH -- ethanol, iPrOH -- propan-2-ol; nPrOH -- propan-1-ol; iPr₂O -- diisopropyl ether; THF -- tetrahydrofuran; CH₃CN -- acetonitrile; Tol -- toluene; CyH -- cyclohexane; Hex - hexane; Hep -- heptane

FIG. 8b

Table 3

| Series (Product) | Substrate | weight [g] | Yield [%] | solvent 1 | V1 [ml] | Solvent 2 | V2 [ml] | Temp. & Conditions | RRT 0.95 | PES-01 1.00 | 1.06 | 1.09 | BAC-01 1.14 | Others RRT, peak area |
|---|---|---|---|---|---|---|---|---|---|---|---|---|---|---|
| *3.1* | *3.0* | *3.52* | *60.6* | *MeOH* | *100* | *AN* | *100* | *boiling* | *3.09* | *78.72* | *0.60* | *0.17* | *1.36* | *1.47 (1.63); 1.53 (3.09); 2.17 (8.50)* |
| 3.2-6 | 3.1 | 0.30 | 60.6 | nPrOH | 10 | water | 10 | Temp of boiling | 0.49 | 96.89 | 0.19 | 0.11 | 1.85 | - |
| 5.0 | | | | | | | | | | | | | | |
| 5-11 | 5.0 | 0.17 | 34.6 | AcOH | 5 | H$_2$O | 1 | 24°C | 3.03 | 87.16 | 0.63 | 2.67 | 5.29 | - |
| 5-12 | 5.0 | 0.41 | 82.4 | AcOH | 5 | H$_2$O | 7 | 80°C | 0.71 | 89.70 | 0.30 | 0.54 | 7.58 | - |
| 5-13 | 5.0 | 0.41 | 81.2 | AcOH | 10 | H$_2$O | 12 | 90-100°C | 0.73 | 88.30 | 1.35 | 0.66 | 6.08 | 1.19 (1.15) |
| 5-14 | 5.0 | 0.33 | 65.0 | AcOH | 10 | H$_2$O | 5 | 90-100°C | 0.59 | 88.74 | 1.29 | 0.21 | 6.52 | 1.19 (2.20) |
| 5-15 | 5.0 | 0.32 | 64.2 | EtCO$_2$H | 10 | H$_2$O | 10 (7.5) | 85-90°C | 0.36 | 85.00 | 1.61 | 1.19 | 7.75 | - |
| 5-16 | 5.0 | 0.28 | 55.0 | EtCO$_2$H | 10 | H$_2$O | 7 | 85-90°C | 0.40 | 90.64 | 0.24 | 0.63 | 7.26 | - |
| | | | | | | | | | 0.85 | 88.28 | 0.48 | 1.28 | 7.50 | 1.19 (0.49) |

FIG. 9a

Table 3 (continued)

| Series (Product) | Substrate [g] | weight [g] | Yield [%] | Solvent 1 | V1 [ml] | Solvent 2 | V2 [ml] | Temp. & Conditions | RRT 0.95 | PES-01 1.00 | 1.06 | 1.09 | BAC-01 1.14 | Others RRT, peak area |
|---|---|---|---|---|---|---|---|---|---|---|---|---|---|---|
| 5-17 | 5.0 | 0.43 | 85.6 | DMF | 10 | H₂O | 10 (4) | 90-100 °C | 1.03 | 88.52 | 0.60 | 2.70 | 6.36 | - |
| 5-18 | 5.0 | 0.35 | 69.0 | DMAc | 10 | H₂O | 5 | 80-90 °C | 0.95 | 89.49 | 0.45 | 1.30 | 7.17 | - |
| 5-19 | 5.0 | 0.34 | 67.8 | NMP | 10 | H₂O | 6 | 80-90 °C | 0.29 | 91.36 | 0.35 | 0.56 | 6.87 | - |
| 5-20 | 5.0 | 0.42 | 84.2 | DMSO | 10 | H₂O | 5 (3) | 80-90 °C | 1.46 | 88.96 | 0.71 | 2.13 | 6.11 | - |
| 5-21 | 5.0 | 0.28 | 56.8 | MeOH | 16 | H₂O | 16 | Reflux | 1.51 | 89.78 | 0.56 | 1.18 | 5.69 | - |
| 5-22 | 5.0 | 0.36 | 71.6 | EtOH | 10 | H₂O | 15 | Reflux | 0.63 | 89.43 | 0.41 | 0.72 | 7.85 | - |
| 5-25 | 5.0 | 0.37 | 74.4 | iPrOH | 11 | H₂O | 12 | Reflux | 0.37 | 92.65 | 0.21 | 0.30 | 5.85 | - |
| 5-26 | 5.0 | 0.38 | 76.8 | MTBE/MeOH | 10/7.5 | H₂O | 10 (5) | Reflux | 0.96 | 90.26 | 0.40 | 0.71 | 6.67 | - |
| 5-28 | 5.0 | 0.30 | 60.8 | MTBE/MeOH | 10/8 | H₂O | 5 (4) | Reflux | 0.73 | 89.79 | 0.22 | 0.42 | 7.76 | - |

MeOH -- methanol; EtOH -- ethanol, iPrOH -- propan-2-ol; nPrOH -- propan-1-ol; AcOH -- acetic acid; EtCO₂H -- propionic acid; DMF -- N,N-dimethylformamide; DMAc - N,N-dimethylacetamide; NMP -- N-methylpyrrolidone; DMSO -- dimethylsulfoxide; MTBE -- tert-butylmethyl ether

FIG. 9b

Table 4

| Series | Substrate | Solvent 1 | V [ml] | Solvent 2 | V [ml] | Temp. [°C] | RRT | | | | | BAC | |
|---|---|---|---|---|---|---|---|---|---|---|---|---|---|
| Product | | | | | | | 0.95 | PES 1.00 | 1.06 | 1.09* | | 1.14 | 1.27 |
| *6.0* | | | | | | | *1.99* | *78.94* | *0.43* | *0.18* | | *12.43* | *0.72* |
| 6.1 | 6.0 | iPrOH | 395 | H₂O | 280 | Reflux | 0.21 | 85.09 | 0.16 | 0.39 | | 13.10 | - |
| 6.2 | 6.1 | iPrOH | 65 | CyH | 250 | Reflux | 0.27 | 95.61 | 0.16 | 0.23 | | 3.53 | - |
| 6.3 | 6.2 | iPrOH | 70 | CyH | 400 | Reflux | 0.32 | 98.50 | 0.13 | 0.15 | | 0.57 | - |

*) impurities of RRT 1.07-1.10, which were visible as two peaks, were not separated and are reported as a sum

FIG. 10

PROCESS FOR THE PREPARATION OF PROTOESCIGENIN

CROSS-REFERENCE TO RELATED APPLICATIONS

This is a continuation-in-part of International Patent Application No. PCT/PL2012/000102, with an international filing date of Oct. 12, 2012, and claims priority benefits to Polish Patent Application No. P-396618, filed Oct. 12, 2011. The contents of all of the aforementioned applications are incorporated herein by reference. The incorporation by reference includes any intervening amendments to the aforementioned applications. Inquiries from the public to applicants or assignees concerning this document or the related applications should be directed to: Matthias Scholl P.C., Attn.: Dr. Matthias Scholl Esq., 14781 Memorial Drive, Suite 1319, Houston, Tex. 77079.

BACKGROUND OF THE INVENTION

1. Field of the Invention

The invention relates to the process for preparation of protoescigenin from escin.

Protoescigenin is a polyhydroxy aglycone obtained during the hydrolysis of escin, the natural saponin present in *Aesculus hippocastanum* seeds. Protoescigenin may be a valuable substrate used in the synthetic modification and derivatization of the naturally occurring saponins.

2. Description of the Related Art

The mixture of saponins known under the common name escin, is the major component of *Aesculus hippocastanum* seeds extracts. It is present in the three forms named α-escin, β-escin and cryptoescin. These saponins belong to polyhydroxy triterpene glycosides, containing four different aglycones (sapogenins), such as escigenin, protoescigenin, barringtogenol C and barringtogenol D, which are characterized by different substituents at the C-16/C-21 and the C-24 hydroxyl groups.

Until now 79 saponins have been isolated and characterized from the hydrolyzates of *Aesculus hippocastanum* seeds extracts. Most of these compounds consist of a trisaccharide chain containing glucuronopyranosyl residue linked via a glycosidic bond to the C-3 atom of an aglycone, acyl groups at the C-21, C-22 and C-28, and seldom at the C-16 position. Acyl moieties embrace angeloyl, tigloyl, acetyl, 2-methylbutanoyl and 2-methylpropanoyl groups (*Pharmaceutical Crops*, 2010, 1, 24-51).

The extracts of *Aesculus* seeds usually vary in composition and the difference depends on a plant species as well as the origin of a plant growth. The chemical composition of saponins isolated from the horse chestnut *Aesculus hippocastanum* L. seeds, growing predominantly in Europe and North America was proposed by R. Tschesche, et al. in *Justus liebigs Ann. Chem.*, 669, 171-182(1963) and can be illustrated by the structure shown in FIG. 6.

The research of Yoshikawa and co-workers resulted in the isolation and identification of 12 saponins, which proved to be the main components of *Aesculus hippocastanum* seeds extracts. The outcome of these works was published inter alia in Chem. Pharm. Bull. 42(6), 1357-1359 (1994); Chem. Pharm. Bull. 44(8), 1454-1464 (1996); *Biol. Pharm. Bull.* 20(10), 1092-1095 (1997), Chem. Pharm. Bull. 46(11), 1764-1769 (1998). The identified compounds included escin Ia, Ib, IIa, IIb, IIIa, IIIb, IV, V and VI and also isoescin Ia, Ib, and V, the chemical structures of which are summarized in the table below.

| Name | Aglycone | $R_1$ | $R_2$ | $R_3$ | $R_4$ | $R_5$ | $R_6$ |
|---|---|---|---|---|---|---|---|
| Escin Ia | PES | H | Tig | Ac | OH | H | Glc-p |
| Escin Ib | PES | H | Ang | Ac | OH | H | Glc-p |
| Escin IIa | PES | H | Tig | Ac | OH | H | Xyl-p |
| Escin IIb | PES | H | Ang | Ac | OH | H | Xyl-p |
| Escin IIIa | BAC | H | Tig | Ac | H | H | Gal-p |
| Escin IIIb | BAC | H | Ang | Ac | H | H | Gal-p |
| Escin IV | PES | H | Ac | Ac | OH | H | Glc-p |
| Escin V | PES | H | MP | Ac | OH | H | Glc-p |
| Escin VI | PES | H | MB | Ac | OH | H | Glc-p |
| Isoescin Ia | PES | H | Tig | H | OH | Ac | Glc-p |
| Isoescin Ib | PES | H | Ang | H | OH | Ac | Glc-p |
| Isoescin V | PES | H | MP | H | OH | Ac | Glc-p |
| Protoescigenin | PES | H | H | H | OH | H | — |
| Barringtogenol C | BAC | H | H | H | H | H | — |

PES—protoescigenin
BAC—barringtogenol C

Escin, due to its beneficial effects on venous tone, anti-inflammatory and anti-edemic activity, is wildly used in medicine, mainly in the treatment of chronic venous insufficiency, but it found use in the cosmetics as well. Although the efficiency of escin has been proved in the traditional medicine as well as in the clinical treatment, the molecular basis of its activity has not been established yet. The complexity of the saponin mixture and the lack of validated analytical methods, necessary for a qualitative and a quantitative determination of the natural compounds composition, impedes studies of pharmacokinetic and biochemical mechanism.

Isolation of the individual saponins from the crude plant material, determination of their structure and their analysis require application of laborious and advanced analytical techniques. These difficulties result from the unique and complex chemical structures of saponins, the similarity of their structure and resulting similar physicochemical properties, for example polarity, and in the end lack of chromophores, which hinders detection of analyzed molecules.

In general, saponins are isolated from the crude plant material by extraction with the mixture of water and an alcohol, such as methanol or ethanol, followed by evaporation of the solvents under reduced pressure, reconstitution of the residue in a small amount of water and separation between n-butanol/water diphase system. For further purifications, the column chromatography techniques or liquid-liquid chromatography separation method are employed, but usually high-performance liquid (HPLC) chromatography must be used. In most cases, obtaining the high purity saponins requires multiple chromatographies, which involves the replacement of column filling and the change of eluting solvents.

For instance, according to the procedure published in *Chem. Pharm. Bull.* 44(8), 1454-1464 (1996), the crude methanolic extract of *Aesculus hippocastanum* L. seeds was chromatographed on Diaion HP-20 column, followed by another separation of methanolic fraction of saponins mixture in reversed phase, on the chromatography column filled with silica gel. Multiple HPLC chromatographies of 90% methanolic eluate containing the pre-purified mixture of saponins furnished separation of escin Ia, Ib, IIa, IIb and IIIa.

In *Justus Liebigs Annalen der Chemie* 1963, 669, 183-188 Kuhn R. and Loew I. described the hydrolysis of escin in the solution of 4 N hydrochloric acid in ethanol, the separation of the intermediate, and its subsequent hydrolysis under basic conditions with potassium hydroxide in methanol. The hydrolysis products were separated by chromatography on silica gel, yielding protoescigenin and escigenin.

Yoshika I. et al. separated and determined the chemical structure of sapogenins isolated from Japanese *Aesculus turbinata* BLUME extract. They also assigned the configuration of carbon atoms bound to hydroxyl groups in ring E of protoescigenin. These findings were published in *Chem. Pharm. Bull.* 19(6), 1200-1213 (1971). According to their procedure, n-butanolic extract of *Aesculus* seeds was condensed in vacuo furnishing a resin residue. This product was refluxed in ether resulting in precipitation of the solid of the crude mixture of saponins, which was subsequently hydrolyzed in 4 N hydrochloric acid in ethanol at elevated temperature. The obtained mixture was diluted with water, condensed and diluted with water again to give a solid precipitate, which was hydrolyzed in the basic medium with 5% KOH methanolic solution. After water addition, the crude mixture of sapogenins precipitated out of the solution, the solid was purified by chromatography on the column filled with aluminum oxide and yielded a mixture of four main compounds. The major sapogenin was purified by crystallization in methanol and precipitated into colorless needles, characterized by a 300-307° C. melting point. The physicochemical data, such as the melting point, IR (KBr) spectra and TLC analyses were consistent with the structure of protoescigenin.

According to the publications identified above, cleavage of the glycosidic bond of deacylated escin occurs during the hydrolysis under acidic conditions. In this process, protoescigenin (deacylated escin II methanolysis), and barringtogenol (deacylated escin III methanolysis) are formed. Under the basic conditions hydrolysis of saponin acyl groups takes place, liberating the molecules of acetic, tyglic and angelic acids.

Although different methods of hydrolysis are well known to those skilled in the art, methods other than chromatography separation of the products of saponin hydrolysis have not been found in the prior art. In all the procedures described in the publications mentioned above, hydrolysis is preceded by chromatographic purification of either the mixtures or individual saponins. Following these multi-step purification processes, some of the pentacyclic triterpenes were successfully isolated and purified on laboratory scale. However, these elaborate and expensive methods cannot be implemented on industrial scale.

The main problem one must face while scaling-up the process, is the viability of the crude extract composition, the similar polarity, and the similarity of molecular weight of the particular saponin mixture components. These physicochemical properties of the crude mixture, as well as the lack of standardization methods designed for the plant raw materials and products, impede the separation of individual saponins either by crystallization or ultrafiltration. Possibility of obtaining protoescigenin of high purity and at bulk quantities is crucial, for the substrate to be used in synthetic modifications. In the molecule of protoescigenin six hydroxyl groups are present. Thus the number of possible products resulting from substitution of hydroxyl groups amounts to 63 ($2^6$–1). This number may dramatically increase if protoescigenin is contaminated with aglycones of other saponins. In the aftermath of chemical reaction, complex mixtures of products of similar structures are formed, the separation of which is impossible.

The results of experimental attempts to produce protoescigenin by the hydrolysis of escin demonstrate that the reaction product is usually the mixture of sapogenins, containing from 40 to 60% of protoescigenin only, as determined by HPLC. Among the other main components of the mixture, barringtogenol C was also detected, accompanied by the smaller amounts of other sapogenins, such as escigenin and barringtogenol D. Methods routinely used for the purification and isolation, for example the multiple crystallization, liquid-liquid or liquid-solid extractions, were not successful in the protoescigenin isolation.

BRIEF SUMMARY OF THE INVENTION

It is the aim of the invention to improve the process of hydrolysis of escin to make possible its implementation at a technical scale, and to develop a method of isolation of protoescigenin from the mixture of sapogenins other than by use of chromatography. It is also the aim of the invention to affect preparation of high purity protoescigenin as the important synthon for further synthetic transformations.

These aims were accomplished through the development of optimal conditions for hydrolysis of escin, effective process of enrichment of the post-hydrolysis mixture of sapogenins with protoescigenin, and selective methods of isolation and purification of protoescigenin.

The invention provides the process for preparation of protoescigenin from escin, comprising:
  a) two-step hydrolysis of escin, consecutively under acidic and basic conditions, resulting in obtaining the crude mixture of sapogenins,
  b) process of enrichment of the crude mixture of sapogenins with protoescigenin, wherein the said process comprises the following steps:
    b-i) dissolving the hydrolysis product in a three-component mixture of solvents to obtain a clear mono- or bi-layer solution,
    b-ii) addition of water to the solution obtained in step b-i), until the precipitation of a solid of the pre-purified mixture of sapogenins containing protoescigenin as the major component occurs,
  c) isolation of the solid obtained in step b-ii),
  d) purification of the pre-purified mixture of sapogenins,
  e) isolation of protoescigenin.

Another embodiment of the invention provides a process for the isolation of protoescigenin having a purity higher than 98% from the mixture of sapogenins, the mixture comprising about 40-60% of protoescigenin, and barringtogenol C, escigenin and barringtogenol D as the main impurities, wherein the process comprises:
  i) dissolving the mixture of sapogenins in a three-component mixture of solvents until clear, mono- or bi-layer solution is formed,
  ii) addition of water to the solution obtained in step i), until the precipitation of a solid of the pre-purified mixture of sapogenins containing protoescigenin as the major component occurs,
  iii) isolation of the solid of the mixture of sapogenins obtained in step ii), containing approximately 70-90% of protoescigenin,
  iv) purification of the solid obtained in step iii) by crystallization, and
  v) isolation of protoescigenin.

Another embodiment of the invention provides a process for the purification of protoescigenin, comprising at least one crystallization in a mixture of solvents comprising an organic solvent and water, and at least one crystallization in a mixture of organic solvents with ethers, acetonitrile, or saturated hydrocarbons.

Another embodiment of the invention is a new compound identified as protoescigenin monohydrate, which has been isolated from the mixture of sapogenins, containing protoescigenin as the main component.

Protoescigenin monohydrate can be prepared by crystallization of protoescigenin in the mixture comprising a $C_1$-$C_3$ alcohol and a saturated hydrocarbon, especially cyclohexane.

BRIEF DESCRIPTION OF THE DRAWINGS

FIG. 7 shows Table 1 which shows results of the crystallization in methanol (comparative Example 15), wherein MeOH is methanol.

FIGS. 8a and 8b show Table 2 which shows results of the crystallization and removal of impurities in solvents selected from group B ('non-polar") (Example 16).

FIGS. 9a and 9b shows Table 3 which shows results of the crystallization and removal of impurities in solvents selected from group A ('polar") (Example 16).

FIG. 10 shows Table 4 which shows results of the purification of the mixture of sapogenins EC-05.T in a multi-step crystallization (Example 17).

DETAILED DESCRIPTION OF THE INVENTION

The invention is illustrated by the following examples, which should not be construed as any limitation of its scope.

Figure 11:
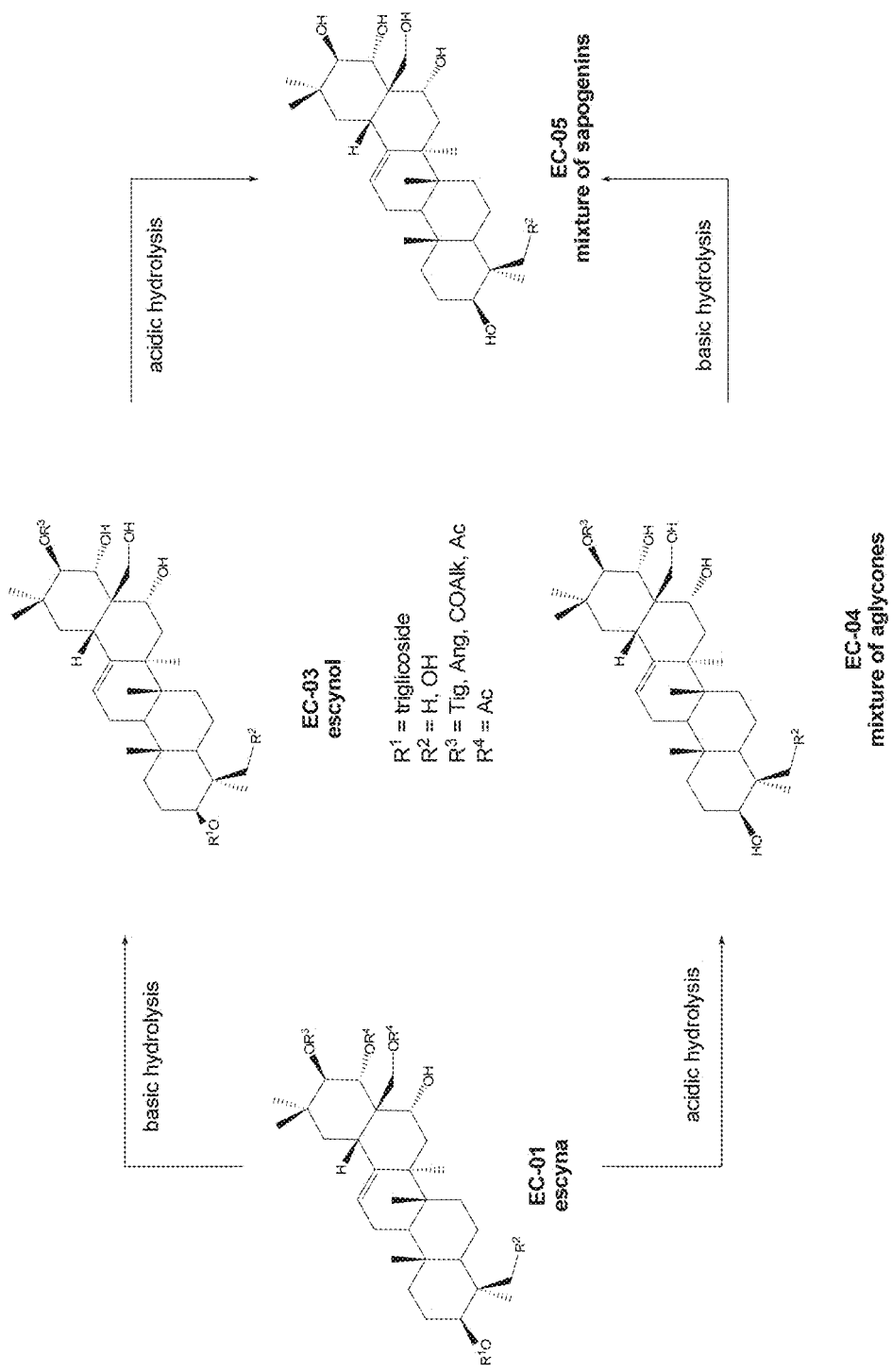
FIG. 11 shows a chemical process according to an exemplary embodiment of the invention.

The process according to the invention is depicted in FIG. 11.

1. Hydrolysis and Separation of the Crude Mixture of Sapogenins

Step a) of the process according to the invention comprises a two-step hydrolysis of escin, isolated from the horse chestnut plant (*Aesculus hippocastanum*), first under acidic and then under basic conditions. The sequence of acidic and basic hydrolyses is optional, but it was proved experimentally that better separation of the crude mixture of sapogenins is achieved when the hydrolysis of escin in an acidic medium is performed prior to hydrolysis in a basic medium.

Preferably, the hydrolysis of escin under acidic conditions is performed for several hours in alcohol, preferably methanol, under reflux, in the presence of an inorganic acid such as sulfuric acid or hydrochloric acid. The product of the hydrolysis precipitates after addition of water. After neutralization of the solution, the solid is filtered, yielding a multi-component mixture of sapogenins and their esters. Temperature increase considerably accelerates the reaction progress and as a result shortens reaction time. At ambient temperature the hydrolysis proceeds very slowly (several days) leaving the substrate not entirely consumed.

The product of acidic hydrolysis is subsequently subjected to hydrolysis under basic conditions in the presence of sodium or potassium hydroxide, in alcohols such as methanol, ethanol, propan-2-ol or the mixture thereof, optionally with the addition of water. The hydrolysis proceeds at a wide range of temperatures. The higher the reaction temperature, the shorter the hydrolysis time.

Preferably, a two-step hydrolysis is a 'one-pot reaction,' without the separation of the intermediate obtained after the acidic hydrolysis.

There are several methods of separation of the hydrolysis products, yielding the crude mixtures of sapogenins of different compositions.

Typically, the solid of the crude mixture of sapogenins (EC-05.S) precipitates out of the reaction medium upon the addition of water; optionally, it is neutralized and washed with water. The product obtained this way is a wet solid in the form of a paste, containing a substantial amount of water (more than 50%, most often 80-90%). It is dried in air or under reduced pressure or it is lyophilized, furnishing a dry solid of EC-05.S, containing less than 10%, for example, about 5-7%, of water.

The crude mixture of sapogenins EC-05.S, obtained in the process according to the invention contains protoescigenin and barringtogenol C as the main products, and minor amounts of other sapogenins with the structures presented below.

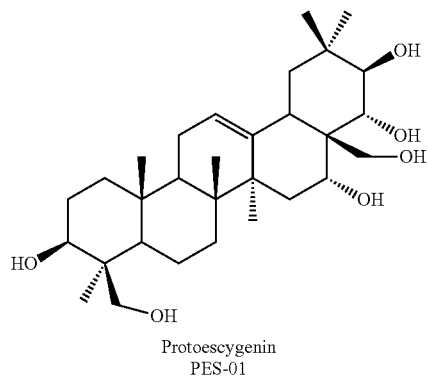

Protoescygenin
PES-01

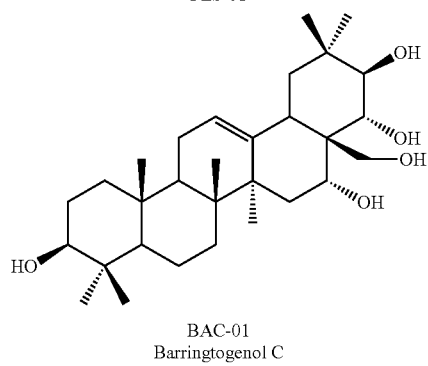

BAC-01
Barringtogenol C

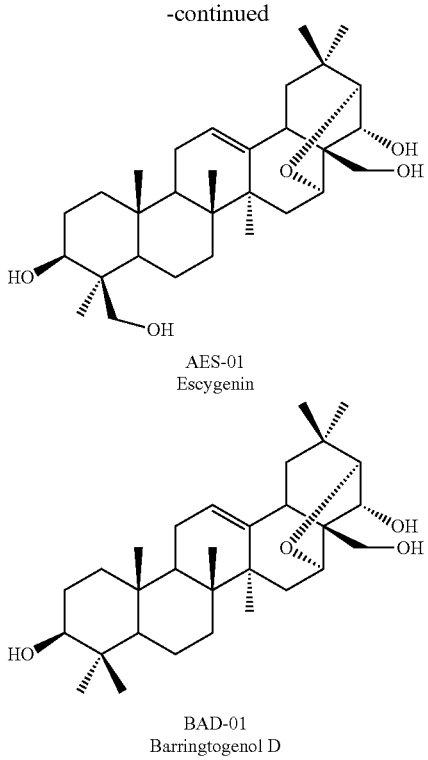

AES-01
Escygenin

BAD-01
Barringtogenol D

According to UPLC analysis, the solid of EC-05.S consists mainly of 40-60% of protoescigenin and 15-25% of barringtogenol C.

2. Preparation of the Pre-purified Mixture of Sapogenins Enriched with Protoescigenin In step b), the crude mixture of sapogenins EC-05.S, obtained in step a) by the hydrolysis of escin, is enriched with protoescigenin.

The process of enrichment with protoescigenin comprises dissolving the crude mixture of sapogenins EC-05.S in a three-component mixture of solvents, until a clear mono- or bi-layer solution is formed (primary solution), followed by the precipitation of the pre-purified mixture of sapogenins by the addition of water and finally separation of the solid enriched with high contents of protoescigenin (EC-05.T), that is more than 70%, most often 75-90%, according to UPLC.

The three-component mixture of solvents used to dissolve the crude mixture of sapogenins comprises:

$C_1$-$C_3$ aliphatic alcohol, as component 1,
water, as component 2, and
a solvent selected from the group comprising aliphatic and cyclic ethers, as component 3.

Preferably, component 1 is methanol, ethanol or propan-2-ol, more preferably methanol.

Component 3 is selected from the group comprising aliphatic ethers such as tert-butylmethyl ether, diisopropyl ether and cyclic ethers such as tetrahydrofuran or dioxane.

Preferably, the crude mixture of sapogenins EC-05.S is enriched with protoescigenin in the three-component mixture of solvents comprising methanol, water, tert-butylmethyl ether.

In another embodiment of the invention, the crude mixture of sapogenins EC-05.S is enriched with protoescigenin in the three-component mixture of solvents comprising methanol, water, diisopropyl ether.

According to the invention, the process of enrichment of the crude mixture of sapogenins EC-05.S with protoescigenin can be performed directly after the second step of the hydrolysis. The mixture can be in the form of a solution or a suspension, in the form of a dry solid obtained by drying or lyophilization or as a wet paste.

Step b) of the invention is accomplished by dissolving the crude mixture of sapogenins in the three-component mixture of solvents, at a temperature ranging from ambient temperature to reflux, and preferably at reflux.

To achieve the best effect, the crude mixture of sapogenins in the three-component mixture of solvents should form a clear mono- or bi-layer solution.

It has been discovered that to obtain the solid enriched with protoescigenin characterized by better physicochemical parameters, the solution must become clear before the nucleation and crystallization take place.

The formation of the mono- or bi-layer solution depends on the physicochemical properties of the solvents used.

Whenever the terms 'bi-layer solution' or 'two phase solution' are used throughout this description, they relate to a mixture of solvents consisting of two separate liquid phases under atmospheric pressure and at a given temperature or at a temperature range from ambient temperature (about 20° C.) to reflux. According to the above definition, a bi-layer solution is not formed by miscible solvents.

In the case when the liquid layers are not separated spontaneously, the addition of an appropriate volume of component 2 and/or component 3 to the mixture facilitates the formation of a bi-layer solution. Undissolved solid materials present in small quantities and/or inorganic solids are separated by filtration.

In step c), the pre-purified mixture of sapogenins EC-05.T enriched with protoescigenin is gradually precipitated from the primary solution, upon the addition of component 2 (i.e., water).

Optionally, the two layers of the primary solution containing the crude mixture of sapogenins EC-05.S are separated, the water layer is washed with selected ether, and the combined organic phases are used for the crystallization of the product. In this process, after the addition of water, a bi-layer solution is formed as well, and a concomitant solid precipitation of the pre-purified mixture of sapogenins EC-05.T occurs.

The solvents of the three-component mixture (primary solution), which is the reaction medium in the crystallization of the pre-purified mixture of sapogenins, are used at different volume ratios. The volumes of solvent components to be used, depend on the contents of the sapogenin mixture. The quantitative ratio of sapogenins in their mixture results from the composition of escin used as the starting material in hydrolysis, hydrolysis conditions, and the presence of some by-products, such as inorganic and organic salts.

In the calculations of the water amount to be used in the three-component mixture that is necessary to dissolve EC-05.S, the water contents of the substrate solid should also be taken into account. As mentioned before, the crude mixture of sapogenins, when used in the form of a suspension or a paste, may contain up to 90% of water.

In general, the mixture comprising methanol-water-tert-butylmethyl ether solvent system, in amounts (given at volume percentage of the mixture) ranging from 15 to 85% of methanol, from 10 to 50% of water and tert-butylmethyl ether up to 100%, provides good solubility of the crude mixture of sapogenins EC-05.S.

In the case when the crude EC-05.S subject to the crystallization is in the form of an aqueous paste, dried solid or lyophilized solid, the volume ratios of solvents are as follows: from 15 to 50% of methanol, from 15 to 40% of water (water amount comprised in the solid was included) and from 20 to 65% of tert-butylmethyl ether, and preferably from 15 to 40% of methanol, from 10 to 35% of water and from 30 to 65% tert-butylmethyl ether. The total volume of solvents, calculated in the relation to the amount of escin used in the hydrolysis, as the EC-05.S equivalent, ranges from 15 mL/g to 60 mL/g, preferably from 20 to 35 mL/g.

When EC-05.S is used in the enrichment process in the form of a solution or a suspension and the separation step of the crude sapogenin mixture from the post-hydrolysis mixture is omitted, the solvents volume ratio ranges from 20 to 70% of methanol, from 10 to 40% of water and from 10 to 50% of tert-butylmethyl ether, preferably from 30 to 70% of methanol, from 15% to 40% of water and from 20% to 50% of tert-butylmethyl ether. The total volume of solvents, calculated in relation to the amount of escin ranges from 40 mL/g to 75 mL/g, and is preferably about 55 mL/g.

In case when the enrichment process subsequently follows the hydrolysis of escin, EC-05.S is used in the form of a solution or a suspension, but inorganic salts formed during hydrolysis are removed by filtration, EC-05.S is not dissolved in the component 3 (the initial amount of ether in the solution accounts for 0%). In such a case, ether is added later to form a three-component solution, in which the precipitation of EC-05.T can proceed according to the method described above.

The water amount required for the precipitation of the solid from the three-component solution in step b) results from the volume proportions of the two other components, reached when the product crystallization occurs. Regardless of the chosen procedure, the final proportion of the solvent amounts includes the total volumes of solvents used in the entire process. The volumes of solvents used before and after the separation of layers are included in these calculations.

In general, the water volume required to precipitate the solid is adjusted experimentally. Usually, in the method without layer separation, a minimum of 20% of water in relation to primary solution total volume is required. It the formation of two layers is followed, precipitation may occur due to the addition of only 10% of volume of water, calculated on the basis of the total volume before separation of phases.

Solid precipitation is performed at temperature values ranging from ambient temperature to reflux. In the process without layers separation, crystallization proceeds at elevated temperatures, at reflux or below. When the method of primary solution liquid phases separation is followed, product precipitates at room temperature.

The manner of water addition to the mixture does not affect process of crystallization. However, slow addition of water is recommended, due to better physicochemical parameters of forming solid (bigger crystals formation) and formation of emulsion is avoided. The beneficial effect on product crystallization, by temperature decreased after water addition was observed. Nucleation of the solution with protoescigenin crystals of purity higher than 98%, and/or addition of another portion of water (⅓ to ½ of initial volume) after precipitation, contribute to yield increase of the process.

The solid separated according to the invention is the pre-purified sapogenins mixture EC-05.T, which is enriched with protoescigenin in comparison with the crude sapogenins mixture EC-05.S. Protoescigenin contents in the mixture amounts from about 70% to 90%.

3. Purification of the Pre-purified Mixture of Sapogenins and Isolation of Crystalline Protoescigenin Regardless the enrichment of the pre-purified mixture of sapogenins EC-05.T with protoescigenin in comparison with the crude hydrolysis mixture EC-05.S, the purity of EC-05.T does not meet the requirements of the substrate used in chemical synthesis. According to UPLC analysis, in protoescigenin solid many impurities were detected, such as barringtogenol C at amount about 5 to 25%, as well as substantial amounts of unidentified impurity characterized by RRT=0.95 (up to 3%).

In step d) according to the invention, to remove plethora of different impurities, the pre-purified mixture of sapogenins EC-05.T is subjected to crystallization in solvents having different physicochemical properties.

Preferably, the pre-purified mixture of sapogenins EC-05.T is purified by at least one crystallization in a mixture of solvents, comprising organic solvent selected from group A with water, and at least one crystallization in a mixture of solvents selected from group B including organic solvents with admixture of ethers or saturated hydrocarbons.

Polar impurities characterized by RRT (RRT=$RT_{analysed\ peak}/RT_{PES-01}$)=0.84, 0.87, 0.95 and 1.06, as well as 'ambient impurities' characterized by RRT=1.09 (there are at least two peaks of the impurity of RRT values ranging from 1.07 to 1.10; separation of these peaks was not successful, therefore they are treated as a total impurity, represented by 1.09 RRT value), especially impurities characterized by RRT=0.95 and 1.09, are effectively removed if the pre-purified mixture of sapogenins EC-05.T is dissolved in a solvent selected from group A, $C_1$-$C_3$ alcohols such as methanol, ethanol, propan-1-ol, propan-2-ol and mixtures thereof with ethers; organic acids such as acetic or propionic acid; amides such as dimethylformamide, dimethylacetamide or N-methylpyrrolidone; and dimethylsulfoxide, at temperature range from ambient temperature to reflux, preferably at elevated temperature, followed by addition of water at ambient temperature or reflux. Solid, precipitating during addition of water or cooling the mixture down, is filtered off, washed with water or the mixture of water and alcohol, and dried.

The impurities characterized by RRT=1.09 and 1.14 (BAC-01) and RRT above 1.14, for example RRT=1.47, 1.53, 2.17, are effectively removed by crystallization in the mixture of solvents selected from group B such as $C_1$-$C_3$ alcohols, i.e., methanol, ethanol, propan-1-ol, propan-2-ol, and the mixtures thereof, as well as their mixtures with acetonitrile, ether, or saturated hydrocarbon, for instance. EC-05.T is dissolved in a selected mixture of solvents at temperature range from ambient temperature to reflux, preferably at elevated temperature. The resulting solution is cooled down or the same amount of alcohol is evaporated.

Another possibility of crystallization is achieved by dissolving the sapogenins mixture EC-05.T in alcohol at reflux, followed by addition of the co-solvent with a concomitant temperature decrease. Preferable co-solvents are ethers such as tetrahydrofuran or diisopropyl ether, or saturated hydrocarbons such as hexane, hexane fraction, cyclohexane, heptane, and also acetonitrile. The isolated solid is washed with a selected solvent and dried.

Purification can be also accomplished by maceration of EC-05.T solid in alcohol or acetone.

The method of purification depends on purity of the starting sapogenins mixture EC-05.T. Application of at least two crystallization processes in different solvents, one crystallization in solvent selected from group A with water and another crystallization in a solvent chosen from group B, yields protoescigenin of purity higher than 98% (according to UPLC), containing less than 1% of barringtogenol C and less than 0.5% of unidentified impurities characterized by RRT=0.95.

The number of crystallizations required to obtain protoescigenin having a purity higher than 98% can be chosen experimentally by those skilled in the art and it is depends on the impurity contents in the pre-purified mixture of sapogenins EC-05.T.

One crystallization in $C_1$-$C_3$ alcohol/water and at least one crystallization in a $C_1$-$C_3$ alcohol/saturated hydrocarbon are much more effective in comparison even with multiple crystallizations of protoescigenin in methanol that had been reported in the literature.

Protoescigenin crystallizes in different polymorphic forms, which are distinguished by variable amount of crystalline water. The different forms have been characterized by X-Ray powder diffraction spectrum data (XRPD). According to *Chem. Pharm. Bull.* 19(6), 1200-1213 (1971) upon crystallization in methanol at least two polymorphic forms of protoescigenin are obtained, which for the purpose of this Application, are denoted as forms II and VI. In these forms, the contents of water range from 1% to 2.8% was determined by thermogravimetric analysis.

Preferably, the compound obtained in the process according to the invention by crystallization in the mixture of propan-2-ol and cyclohexane is isolated in the form of protoescigenin monohydrate, named Form III.

Protoescigenin monohydrate is a new compound, having characteristic peaks in X-ray powder diffraction (XRPD) pattern recorded with CuKα, λ=1.54056 Å, having the specific diffraction lines at diffraction angles 2θ of about 6.74; 8.45; 11.17; 13.61, and 14.57±2°.

Protoescigenin monohydrate has characteristic peaks in the X-ray powder diffraction (XRPD) pattern recorded with CuKα, λ=1.54056 Å, presented by the reflection angles 2θ [°], interplanar spacings d [Å] and relative intensities in relation to the most intensive diffraction peak, $I/I_0$ [%], as set forth below:

| 2θ | d | $I/I_0$ |
|---|---|---|
| 6.74 | 13.109 | 17 |
| 8.45 | 10.451 | 5 |
| 11.17 | 7.916 | 7 |
| 13.61 | 6.502 | 52 |
| 14.57 | 6.076 | 100 |
| 16.34 | 5.422 | 10 |
| 16.91 | 5.240 | 16 |
| 18.98 | 4.671 | 11 |
| 21.02 | 4.223 | 12 |
| 22.41 | 3.963 | 5 |
| 24.02 | 3.702 | 5 |
| 27.19 | 3.277 | 6 |
| 28.58 | 3.121 | 9 |

Figure 1:
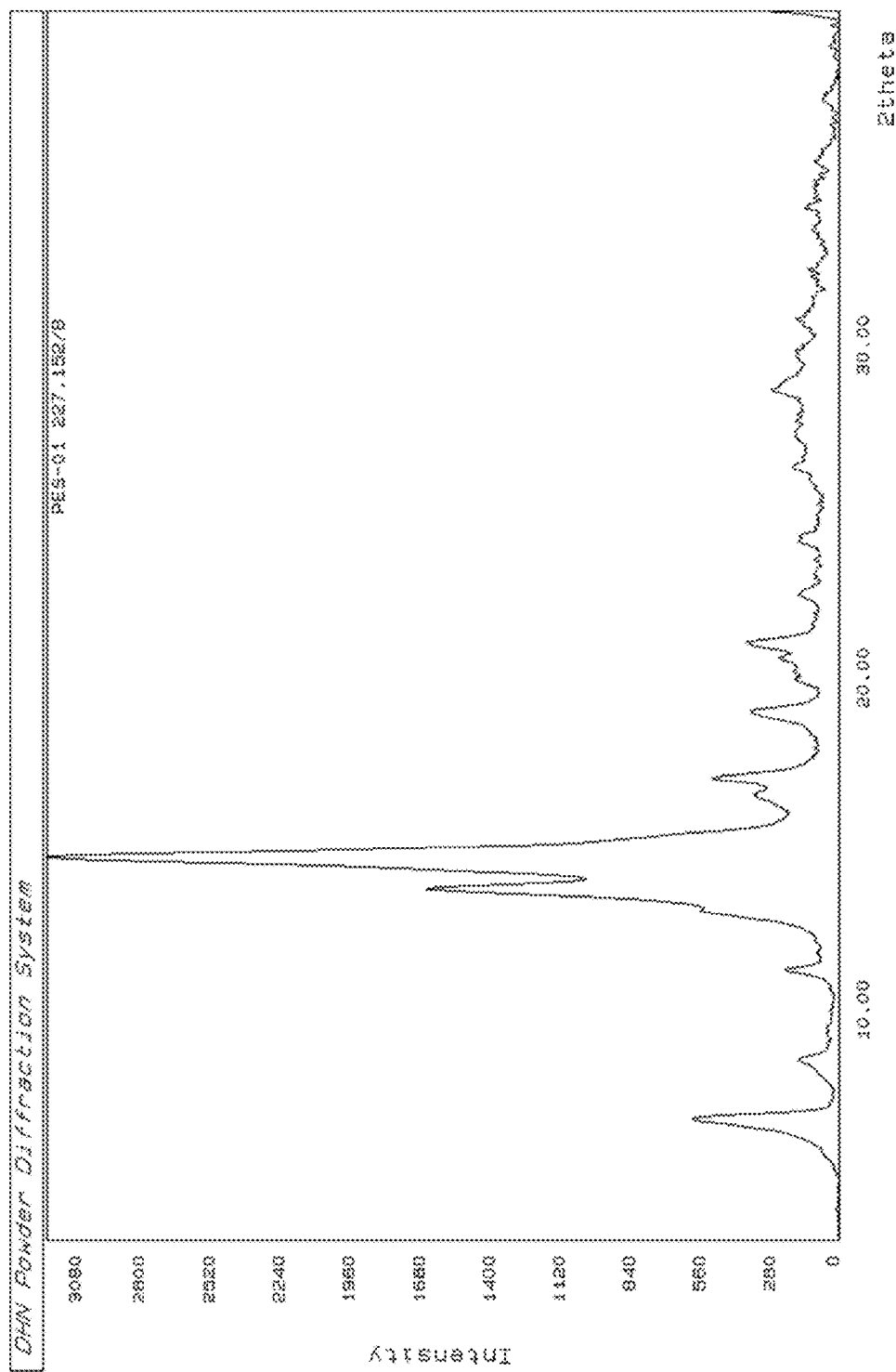
FIG. 1 shows an X-Ray powder diffraction spectrum of protoescigenin monohydrate.

Representative X-ray powder diffraction spectrum of protoescigenin monohydrate is depicted in FIG. 1.

Figure 2:
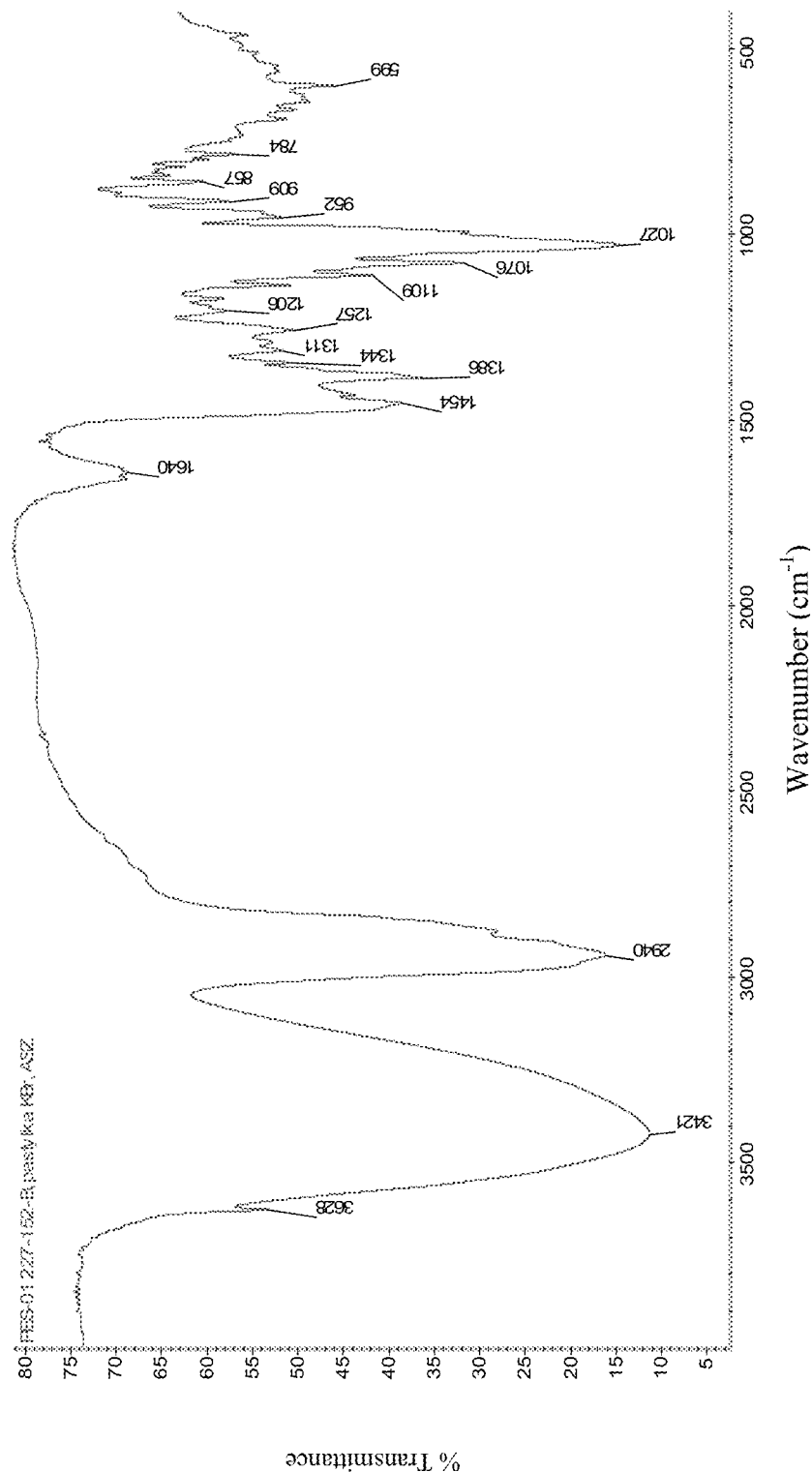
FIG. 2 shows an IR spectrum (KBr) of protoescigenin monohydrate.

Infrared spectrum of protoescigenin monohydrate, performed in a KBr pressed tablet, is depicted in FIG. 2.

Figure 3:
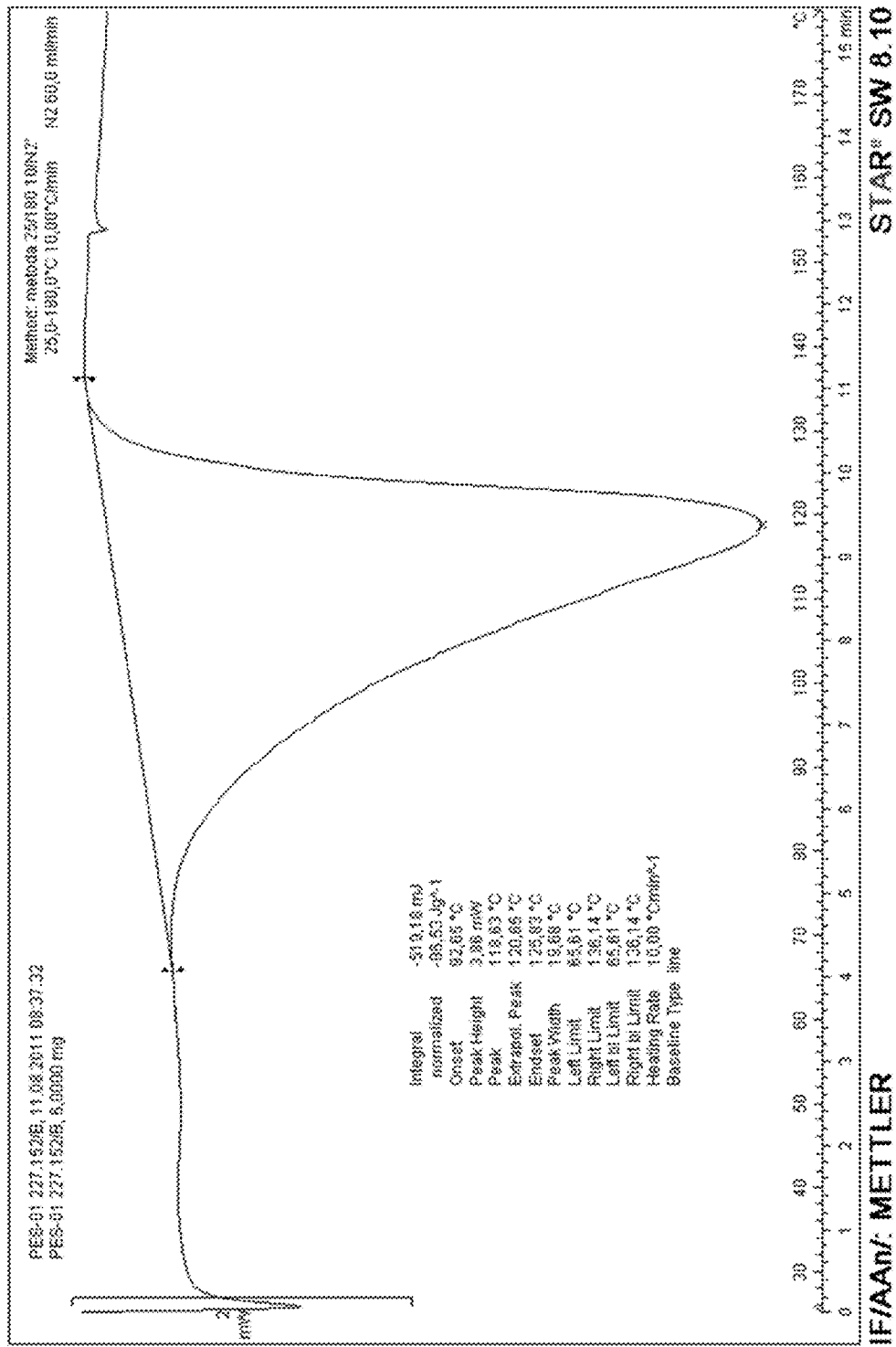
FIG. 3 shows a DSC of protoescigenin monohydrate.

DSC profile of protoescigenin monohydrate recorded by differentiation scanning calorimetry is presented in FIG. 3, and is characterized by two specific endothermic effects. The first effect, observed at 98.86° C. is the melting point determined as the onset (onset), with enthalpy of 100.60 J/g, and comes from the elimination of water of crystallization. The second effect, observed at 319.37° C. (onset) with enthalpy of 58.80 J/g, comes from the melting of substance with accompanying decomposition.

A thermogravimetric curve (solid line in FIG. 2) shows a visible weight loss within the temperature range from 30 to 150° C. Another weight loss is from 320° C. The comparison of effects from TGA, SDTA (Single Differential Thermal Analysis; dashed line) and DSC curves proves that first effect results from a solvent evaporation and the second one is from the decomposition of substance.

Figure 4:
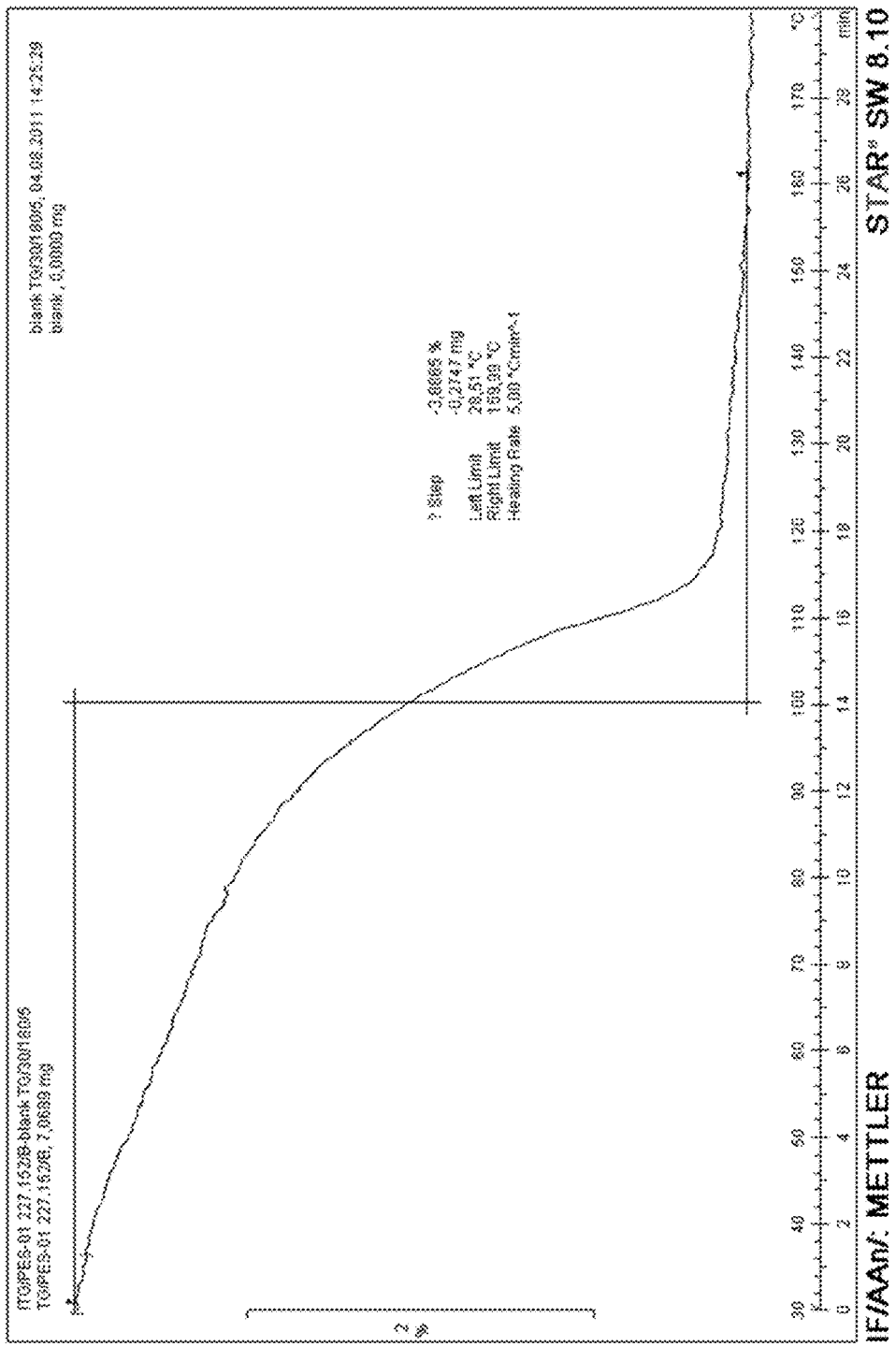
FIG. 4 shows a thermogravimetric analysis (TGA) of protoescigenin monohydrate.

In the TGA curve, measured with the scan speed of 5° C./min, a weight loss of 3.67% calculated to 160° C. was determined (FIG. 4). This mass loss is observed on the DSC curve as a first endotherm. The percentage value of weight loss and amount of water determined by the Karl Fischer method, correspond to stoichiometric amount of water contained in protoescigenin monohydrate crystals, which is 3.43%.

Protoescigenin monohydrate is stable under ambient conditions, up to 100° C. X-ray diffraction measurements of monohydrate were done at the following temperature loop: 25° C.→30 min at 110° C.→25° C. It has been observed that form III after heating for 30 min at 110° C. changes to a different form, called form V.

Figure 5:
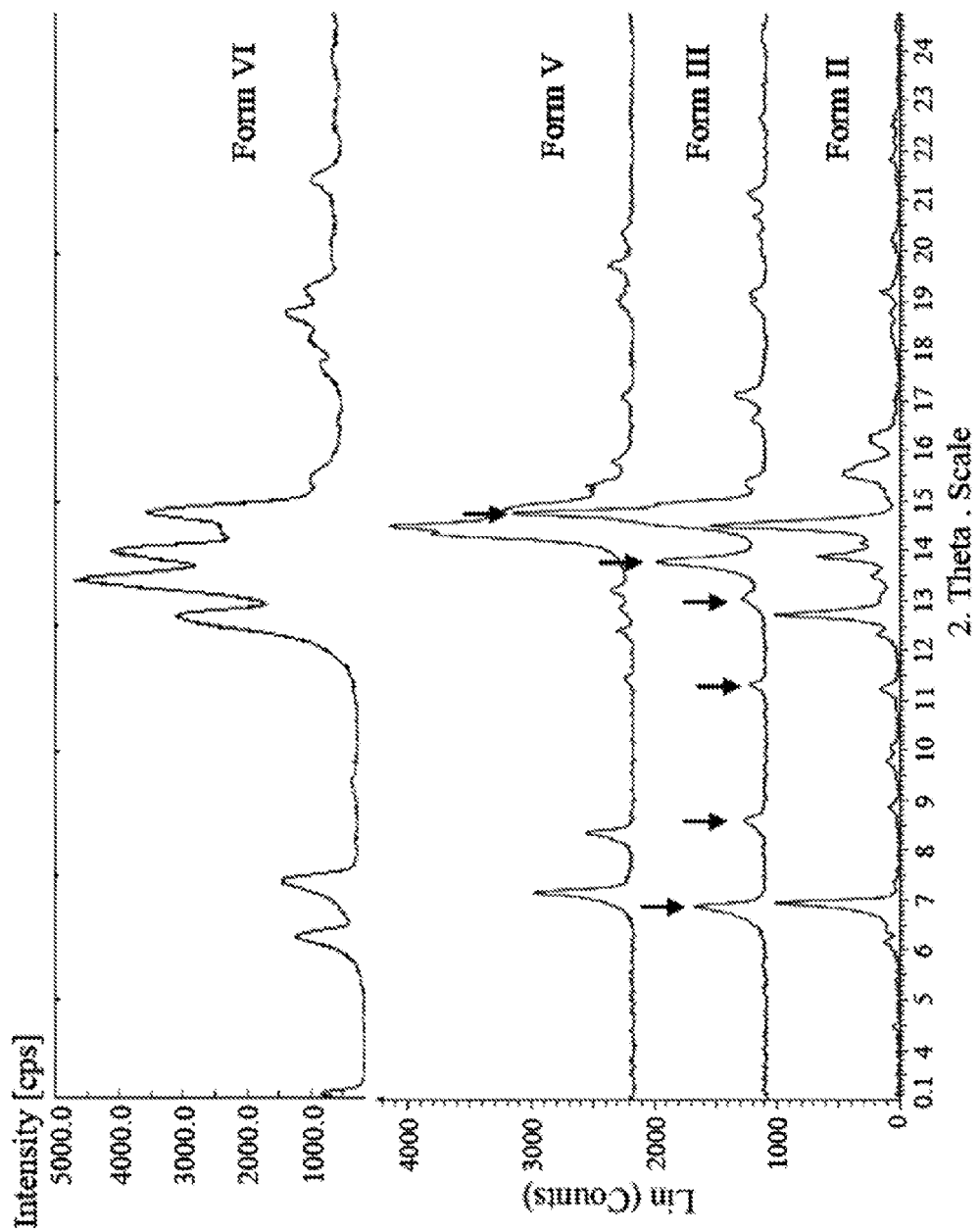
FIG. 5 shows an XRPD of II, III, V and VI forms of protoescigenin. The arrows point to the characteristic peaks of protoescigenin monohydrate (form III).
Figure 6:
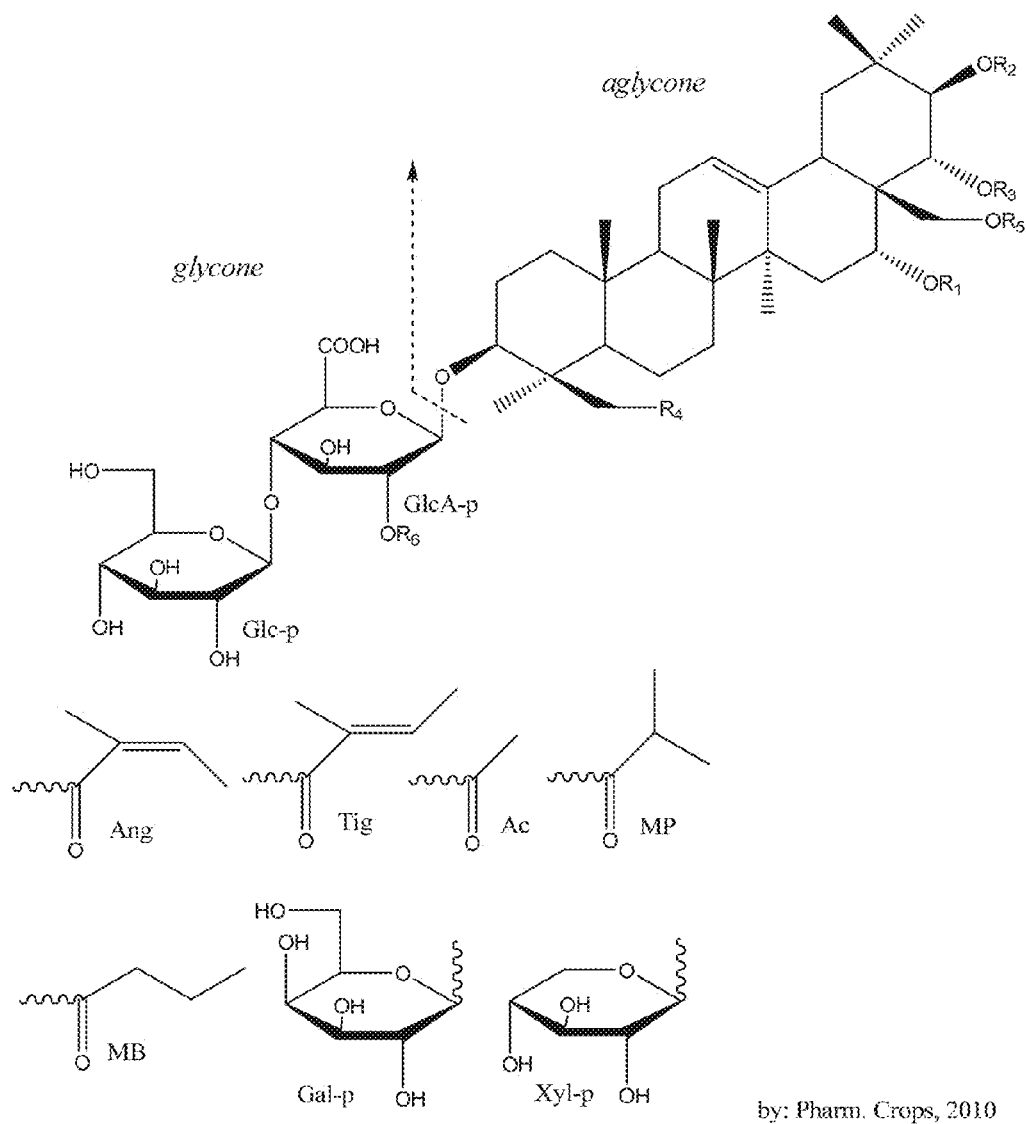
FIG. 6 illustrates a chemical structure of saponins isolated from the horse chestnut *Aesculus hippocastanum* L. seeds, as proposed by R. Tschesche, et al. in *Justus Liebigs Ann. Chem.*, 669, 171-182 (1963), wherein Ang is angeloyl, Tig=tigloyl, Ac=acetyl, MP=2-methylpropanoyl, MB=2-methylbutanoyl, GlcA-p=β-D-glucuronopyranosyl acid, Glc-p=β-D-glucopyranosyl, Gal-p=galactopyranosyl, Xyl-p=β-D-xylopyranosyl.

According to TGA measurements, Form V contains from 1.35 to 1.65% of water which is consistent with the stoichiometric water content in the hemihydrate form (1.75%). Form V is characterized by a different X-ray powder diffraction spectrum from the ones obtained for forms II and VI and as well as form III of protoescigenin monohydrate. The diffraction spectrums of the mentioned forms are compared in FIG. 5. Forms II and VI contain from about 1 to 2.8% of water as well as from monohydrate form III. Diffraction spectrums of the different protoescigenin crystalline forms are compared in FIG. 5.

The invention enables the preparation of protoescigenin of purity higher than 98% by means of hydrolysis of naturally available escin, enrichment of the resulting crude mixture of sapogenins in protoescigenin and purification thereof by crystallization, without the need of laborious chromatography technique.

The invention is further illustrated by the following preparative examples.

EXAMPLES

Analytical Methods

The IR spectrum was recorded on the Bruker Alpha spectrometer in the range of 4000-400 cm$^{-1}$, with spectral resolution of 4 cm$^{-1}$. Samples were measured in KBr pellets (about 1.5 mg of substance/200 mg KBr).

The $^1$H and $^{13}$C NMR spectra were acquired on the Varian VNMRS 600 spectrometer at 600 MHz transmitter frequency.

X-ray powder diffraction (XRPD) studies were performed by means of the MiniFlex diffractometer (Rigaku Coporation, Tokyo Japan) using CuKα radiation (λ=1.54056 Å) with following parameters:

Scanning range 2θ: from 3° to 40°
Scanning speed: 0.5°/min
Measurement step: 2θ: 0.02°
Measurement temperature: ambient temperature
Detector: scintillator Diffraction spectrums were analyzed using the DHN_PDS software.

Differential scanning calorimetry (DSC) measurements were carried out by means of the DSC822 with IntraCooler (Mettler Toledo) with following parameters:

Pan: aluminum 40 μL
Atmosphere: $N_2$, 60 mL/min

Measurement: heating from 25 to 350° C. at 10° C./min
Sample preparation: accurately weighed samples (5-7 mg) were packed in the aluminum pan with the pierced lid.
Thermogravimetric analyses (TGA) were carried out by means of the TGA/SDTA851e (Mettler Toledo) with following parameters:
Pan: aluminum 40 μL
Atmosphere: $N_2$, 60 mL/min
Measurement: heating from 30 to 400° C. at 10° C./min and heating from 30 to 180° C. at 5° C./min. Measurements were blank curve corrected.
Sample preparation: accurately weighed samples (5-7 mg) were packed in the aluminum pan with the pierced lid.
Water content determination was done by the Karl Fischer volumetric titration, according to Ph. Eur. 2.5.12, using the Methrom 701 KF Titrino apparatus and the Methrom 6.0338.100 electrode.
Specific rotation was calculated from an optical rotation measurement performed on the PERKIN ELMER 341 polarimeter at the wavelength of 589 nm (sodium lamp), at 20° C. A sample was dissolved in methanol (HPLC purity).
Related substances determination using Ultra Performance Liquid Chromatography (UPLC) was carried out employing UHPLC Dionex Ultimate 3000, equipped with PDA detector.
Method parameters:
UPLC Acquity BEH C18 2.1×50 mm, 1.7 μm column
Column temperature 30° C.
Mobile chase flow: 0.5 ml/min
Injection Volume: 2 μl
Detection wavelength 200 nm
Sample concentration: 2 mg/ml
Diluent: MeOH, UPLC purity
Mobile chase A: 10 mM ammonium acetate, pH 6.8, UPLC purity
Mobile chase B: acetonitrile, UPLC purity

| T [min] | % A | % B |
|---|---|---|
| 0 | 80 | 20 |
| 4.7 | 0 | 100 |
| 8 | 0 | 100 |
| 8.1 | 20 | 80 |
| 9.5 | 20 | 80 |

Mass spectrometry analysis was carried out using Applied Biosystems QTrap 3200, equipped with ESI ion Skurce. 0.1% solution of ammonium acetate in MeOH was used as a diluent. Sample concentration was 0.1 mg/ml Example 1

Internal Experiment ID: 227.041
β-Escin (commercially available) (100 g) was dissolved in MeOH (350 mL) at RT (23° C.). Concentrated $H_2SO_4$ (40 mL) in MeOH (60 mL) was added dropwise to the obtained solution. The resulting clear reaction mixture was refluxed for 1 h 30 min. Heating was removed and 30% NaOH solution (190 mL) was slowly added dropwise in at 50° C. The temperature was raised to 70° C. and the reaction mixture was further stirred at this temperature for 20 min. Upon $H_2O$ (600 mL) addition, fine-crystalline solid precipitated. The solid was filtered off and washed with $H_2O$ (4×200 mL). A creamy solid was obtained as a paste (water content 84%, by Karl-Fischer); yield 465 g, UPLC: 55.3% PES-01; 24.8% BAC-01.

Example 2

β-Escin (commercially available) (10 g) was dissolved in MeOH (40 mL) at RT (23° C.). $HCl_{aq}$ (35%, 7 mL) in MeOH (6 mL) was added dropwise to the obtained solution. The resulting clear reaction mixture was refluxed for 1 h 30 min. Heating was removed and 25% $NH_{3\,aq}$ solution (190 mL) and 30% NaOH aq. (13 mL) solution were slowly dropped in at 50° C. The temperature was raised to 60° C. and the reaction mixture was further stirred at this temperature for 20 min. Upon $H_2O$ (150 mL) addition, fine-crystalline solid precipitated. The solid was filtered off and washed with $H_2O$ (3×100 mL). A creamy solid was obtained as a paste.

Example 3

Internal Experiment ID: 227.047
The wet solid obtained in Example 1 (41.6 g) was dissolved in a mixture of MeOH (125 mL), tert-butylmethyl ether MTBE (125 mL) and $H_2O$ (50 mL) at reflux. Heating was removed and to the hot solution MTBE (100 mL) and $H_2O$ (40 mL) were added. The resultant clear, bi-layer solution was allowed to cool down to 30° C. The phases were separated, organic phase was transferred to a flask and water (25 mL) was added at RT (23° C.). Crystalline white solid precipitated from the reaction mixture. The mixture was stirred for some hours. Then, the solid was filtered off and washed with water. The solid was dried overnight in the laboratory drier at 45° C. Yield 2.0 g, UPLC: 87.6% PES-01; 5.1% BAC-01.

Example 4

Internal Experiment ID: 227.065
The dried solid obtained in Example 1 (7.60 g; 16.3% of solid obtained from 100 g of escin) was dissolved in the mixture consisting of MeOH (125 mL), MTBE (125 mL) and $H_2O$ (90 mL) at reflux. Heating was removed and to the hot solution MTBE (100 mL) and $H_2O$ (50 mL) were added. The clear, bi-layer solution was allowed to cool down to 25° C. The phases were separated; organic phase was extracted with MTBE (2×50 mL). Combined organic phases were transferred to a flask and water (25 mL) was added at RT (23° C.). After several minutes, the crystalline white solid precipitated from the reaction mixture. The mixture was stirred for further 15 min, then the additional portion of water was added (25 mL) and the mixture was left overnight. The precipitated solid was filtered off and washed with water and acetonitrile. The product was dried in the laboratory drier overnight at 45° C. Yield 2.67 g, UPLC: 86.1% PES-01; 6.27% BAC-01.

Example 5

Internal Experiment ID: 227.051
The dried solid having a water content of 8.26%, UPLC: 46.1% PES-01, 16.0% BAC-01, in the amount 7.60 g (18% of the solid obtained from 100 g of escin) was dissolved in the solvents mixture consisting of MeOH (125 mL), MTBE (125 mL) and $H_2O$ (90 mL) at reflux. Heating was removed and to the hot solution MTBE (100 mL) and $H_2O$ (30 mL) were added. The clear, bi-layer solution was allowed to cool down to 25° C. The phases were separated, organic phase was transferred to a flask and water (25 mL) was added at RT (23° C.). The crystals of pure protoescigenin (UPLC: 98%) were added to the obtained suspension. After several minutes, the crystalline white solid precipitated from the reaction mixture. The mixture was stirred for further 15 min; then further portion of water was added (10 mL) and the mixture was left overnight. The solid was filtered off and washed with water and acetonitrile. The product was dried in the laboratory drier overnight at 45° C. Yield: 1.90 g, UPLC: 89.5% PES-01; 4.7% BAC-01.

Example 6

The crystalline β-escin (200 g) was dissolved in 700 mL of MeOH at RT. Then concentrated $H_2SO_4$ (80 mL) was added dropwise to within ca. 20 min., and the addition funnel was rinsed with 100 mL MeOH. During the course of dropping the temperature of the solution was raised from 24 to 45° C. Heating was turned on and the reaction mixture was refluxed for ca. 3 h, when the reaction was monitored by TLC (AcMe-$H_2O$ 8:1). It was left overnight to cool down.

Water (3.0 L) and KOH (100 g) were placed in the flask. The mixture was heated to 45-50° C. Post-reaction solution, after rinsing the flask with 100 mL MeOH, was put in the addition funnel and added dropwise to the flask within 10 min, while stirring vigorously. pH of the reaction mixture was adjusted to pH 7 by the use of 30% $KOH_{aq}$. The slurry was cooled down. The solid was filtered off and washed with water (3×200 mL). The obtained solid EC-04 (136 g) was dried in vacuo over $P_2O_5$ for 2 days, resulting in 110.5 g of the product EC-04.

Part of the obtained solid EC-04 (55.3 g) was placed in a 1.5 L reactor equipped with a reflux condenser, a magnetic stirrer, and a heater, and dissolved in methanol (250 mL). Then, a solution of KOH (24.3 g) in methanol (250 mL) was added and the reaction was heated under reflux for 4-5 h (monitoring by TLC, AcOEt-MeOH 9:1 or $CHCl_3$—AcOEt-MeOH 45:45:10). It was left overnight to cool down.

The reaction mixture was added to a 4.5 L reactor equipped with stirrer and an addition funnel filled with 2 L of water, while stirring vigorously. White solid precipitated. The suspension was neutralized to pH 7.5-8.0 by the addition of 3M HCl solution. The reaction was stirred for 2 h; then, it was transferred into a Schott's funnel. The equipment and solid were washed with water (1×200 mL) under reduced pressure, and the solid was additionally washed with water (2×200 mL). Then, the suspension was diluted with water and lyophilized overnight. The obtained product was dried in the vacuum drier ($P_2O_5$, 45° C., 1 day), to obtain 36.6 g of the lyophilized mixture of sapogenins EC-05.S having the water content 5.1%, UPLC purity: 48.6% PES-01, 16.1% BAC-01.

Internal Experiment ID: 227.067

EC-05.S lyophilizate (7.10 g; 9.3% of the solid obtained from 100 g of escin) was dissolved in a mixture consisting of MeOH (130 mL), MTBE (110 mL), and $H_2O$ (95 mL) under reflux. Heating was removed and to the hot solution a portion of MTBE (140 mL) and $H_2O$ (45 mL) were added. A clear, bi-layer solution was left overnight to cool down to 25° C. The layers were separated, the organic phase was transferred to the flask and water (50 mL) was added at RT. After several minutes, a white solid precipitated from the reaction mixture. After 15 min of stirring, an additional portion of water was added (25 mL) and the reaction was left overnight.

EC-05.T solid was filtered off, washed with water and acetonitrile and dried in the laboratory drier overnight at 45° C. Yield: 2.17 g, UPLC: 83.9% PES-01; 3.4% BAC-01.

Example 7

Internal Experiment ID: 226.003

The concentrated $H_2SO_4$ (8 mL) w MeOH (12 mL) was added to the solution of β-escin (20 g) in MeOH (60 mL) at RT. A strong exothermic effect was observed. The addition funnel was washed with MeOH (6 mL). The entire solution was stirred under reflux for ca. 2 h (TLC monitoring, $SiO_2$, $CHCl_3$-MeOH-water 16:8:1).

The solution was cooled down to ca. 40-50° C. and the solution of NaOH (15.2 g) in water (35.5 mL) was added, while observing a strong exothermic effect. The resulting yellow-orange suspension was stirred under reflux for ca. 2 h (TLC monitoring, $CHCl_3$—AcOEt-MeOH 45:45:10). The suspension was cooled down and filtered. The solid was washed with MeOH (2×50 mL) and discarded. The resulting filtrate was transferred to the reactor and heated to ca. 50-55° C. MTBE (300 mL) was added and then water (500 mL) was slowly added dropwise in while keeping the temperature above 50° C., until the solid occurred on the phase boundary. The additional amount of 100 mL of water was added dropwise. The suspension was left overnight to cool down. The solid was filtered off, washed with water (2×50 mL) and acetonitrile (2×30 mL). After drying, 3.41 g of the solid EC-05.T was obtained, UPLC: 86.9% PES-01; 2.77% BAC-01.

Example 8

The wet solid EC-05.S (21 g; 5.8% of the solid obtained from 100 g of β-escin, water content ca. 80%, UPLC: 51.2% PES-01, 19.8% BAC-01) was dissolved in the mixture consisting of MeOH (30 mL), tetrahydrofuran THF (40 mL) and $H_2O$ (10 mL) under reflux. Heating was removed, to the hot solution a portion of $H_2O$ (40 mL) was added and the mixture was seeded with pure PES-01 (UPLC 98%). The additional amount of $H_2O$ (25 mL) was added. When the white solid precipitated, the suspension was left overnight to cool down. The solid was filtered off, and washed with $H_2O$ and acetonitrile. The solid was dried at 50-55° C. for 16 h. Yield: 827 mg, UPLC: 70.12% PES-01, 24.14% BAC-01.

Example 9

The wet solid EC-05.S (42 g; 10.6% of the solid obtained from 100 g of β-escin, water content ca. 80%, UPLC 51.2% PES-01, 19.8% BAC-01) was dissolved in the mixture consisting of MeOH (90 mL), diisopropyl ether DIPE (50 mL) and $H_2O$ (15 mL) under reflux. An additional amount of DIPE (100 mL) was added, forming two layers and the mixture was left to cool down. The layers were separated, $H_2O$ (75 mL) was added dropwise to the ether layer at RT while stirring vigorously. Two layers separated and the white solid precipitated out. The suspension was stirred for 1 h and an additional amount of water (25 mL) was added. The suspension was left overnight. The solid was filtered off, washed with $H_2O$ and acetonitrile. The solid of EC-05.T was dried overnight in a vacuum drier at 40° C. Yield: 2.64 g, UPLC: 92.7% PES-01, 2.8% BAC-01.

Example 10

The wet solid of EC-05.S (19.5 g, obtained from β-escin according to the procedure of Example 1, UPLC 59.4% PES-01, 19.5% BAC-01) was dissolved under reflux in a mixture consisting of EtOH (100 mL), MTBE (100 mL), and $H_2O$ (100 mL). A portion of MTBE (75 mL) was added to the clear solution, resulting in a two layer formation. Heating was removed and the solution was left to cool down to RT. The layers were separated. $H_2O$ (40 mL) was added to the ether solution at RT while stirring vigorously. Two layers were formed and a white solid precipitated. The suspension was stirred for 1 h and an additional amount of water (15 mL) was poured in. The suspension was left overnight. The solid was filtered off, washed with water and acetonitrile. The solid of EC-05.T was dried at 50-55° C. for 16 h. Yield: 1.96 g, UPLC: 71.10% PES-01, 20.87% BAC-01.

The solid was dried at 50-55° C. for 16 h. Yield 0.57 g of EC-05.T, UPLC: 79.40% PES-01, 4.52% BAC-01.

Example 11

Internal Experiment ID: 227.131

The wet solid of EC-05.S (42 g, obtained from 10 g of β-escin according to the procedure of Example 1, UPLC: 48.3% PES-01, 19.5% BAC-01) was dissolved in the mixture consisting of i-PrOH (30 mL), MTBE (30 mL), and $H_2O$ (100 mL) under reflux. A portion of $H_2O$ (50 mL) and MTBE (30 mL) were further added to the clear solution, resulting in a two layer formation. Heating was removed, then the solution was left to cool down to RT and it was further stirred at the same temperature for 20 min. White solid precipitated at the phase boundary. It was filtered off and washed with $H_2O$ (50 mL). The solid of EC-05.T was dried at 50-55° C. for 16 h. Yield: 0.57 g, UPLC: 79.40% PES-01, 4.52% BAC-01.

Example 12

Internal Experiment ID: 226.063, Method Dallas-1

Concentrated $H_2SO_4$ (40 mL) in MeOH (300 mL) was added to the solution of β-escin (100 g) in MeOH (50 mL) at RT. The addition funnel was washed with MeOH (50 mL). The resulting solution was stirred under reflux for ca. 2 h (TLC monitoring, $SiO_2$, $CHCl_3$-MeOH-water 16:8:1).

The solution was cooled down to ca. 40-50° C. and a solution of NaOH (76 g) in water (175 mL) was added. The resulting yellow-orange suspension was stirred under reflux for ca. 2 h (TLC monitoring, $CHCl_3$—AcOEt-MeOH 45:45: 10). To the heated suspension, MeOH (850 mL), MTBE (1250 mL), and water (525 mL) were added. A clear, bi-layer solution was formed. After an additional portion of water was added (650 mL), heating was stopped and the solution was cooled down. After ca. 10 min white solid precipitated out. An additional amount of water (500 mL) was added dropwise. The suspension was heated for ca. 1 h and was left overnight to cool down. The solid was filtered off, washed with several portions of $H_2O$ (750 mL in total) to adjust the pH of the filtrate to below pH 8.0, and then the solid was washed with acetonitrile (1×150 mL). After drying, 22.1 g of a solid EC-05.T was obtained, UPLC: 87.2% PES-01; 5.3% BAC-01.

Example 13

The concentrated $H_2SO_4$ (6 mL) in MeOH (50 mL) was added to the solution of β-escin (20 g) in MeOH (15 mL) at RT. The addition funnel was washed with MeOH (15 mL). The resulting solution was stirred under reflux for ca. 2 h (TLC monitoring, $SiO_2$, $CHCl_3$-MeOH-water 16:8:1).

The solution was cooled down to ca. 40-50° C. and the solution of NaOH (11.2 g) in water (35.5 mL) was added. The resulting yellow-orange suspension was stirred under reflux for ca. 2 h (TLC monitoring, $CHCl_3$—AcOEt-MeOH 45:45: 10). To the heated suspension MeOH (210 mL), diisopropyl ether (250 mL), and water (300 mL) were added. An additional portion of water was added dropwise to (300 mL). Heating was stopped and the solution was cooled down to RT. During the course of cooling, white solid precipitated. The suspension was heated for ca. 1 h and was left overnight to cool down. The solid was filtered off, washed with $H_2O$ (2×100 mL) to adjust pH of the filtrate below pH 8.0, and then the solid was washed with acetonitrile (2×25 mL). After drying at 45° C., 5.61 g EC-05.T was obtained; UPLC: 70.11% PES-01; 20.46% BAC-01.

Example 14

Concentrated $H_2SO_4$ (8 mL) in MeOH (10 mL) was added to the solution of β-escin (20 g) in MeOH (60 mL) at RT. The addition funnel was washed with MeOH (10 mL). The resulting solution was stirred under reflux for ca. 2 h (TLC monitoring, $SiO_2$, $CHCl_3$-MeOH-water 16:8:1).

The solution was cooled down to ca. 40-50° C. and a solution of NaOH (15.2 g) in water (35.5 mL) was added. A strong exothermic effect was observed. The resulting yellow-orange suspension was stirred under reflux for ca. 2 h (TLC monitoring, $CHCl_3$—AcOEt-MeOH 45:45:10).

MeOH (120 mL) and MTBE (220 mL) were added to the heated suspension. Then, water was slowly added dropwise. After adding 185 mL of water, a clear bi-layer solution was obtained. The solution was cooled down to 30° C. The layers were separated, to give an aqueous phase (1) and an organic phase (1). To the water phase (1), MTBE (100 mL) and MeOH (70 mL) were added dropwise, and the mixture was stirred vigorously for 10 min. The phases were separated to give an aqueous phase (2) and an organic phase (2).

Organic phase (1) was placed in the flask and water (30 mL) was added dropwise at RT (ca. 24 C). A solid precipitated. After stirring, an additional amount of water (20 mL) was added. The reaction mixture was stirred overnight. The solid was filtered off, washed with $H_2O$-MeOH solution (7:3, 2×50 mL) and with acetonitrile (25 mL). After drying overnight at 45° C., white solid EC-05.T, 2.99 g was obtained; UPLC: 89.6% PES-01; 1.0% BAC-01.

Comparative Example 15

Series 1.0 (Table 1)

EC-05.T was subject to some crystallization in methanol, according to the following description.

Internal Experiment ID: 220.106, 220.124, and 220.142

1.1-1. A mixture of sapogenins EC-05.T (6.1 g; UPLC: 73.83% PES-01, 3.66% BAC-01, 11.65% of impurity of RRT 2.17), was dissolved in MeOH (200 mL) and was allowed to cool down. The obtained solid was filtered off and washed with acetonitrile (3×12 mL). 3.65 g (59.9%) of solid 1.1-1 was obtained; UPLC: 3.23% RRT (0.95), 78.51% PES-01, 1.11% BAC-01.

1.2-1. Solid 1.1-1 (3.56 g) was dissolved in MeOH (131 mL) under reflux and was allowed to cool down to RT. The obtained solid was filtered off, washed with cold MeOH (3×10 mL) and dried. Solid 1.2-1, 1.97 g (55.34%) was obtained; UPLC: 4.28% RRT(0.95), 90.39% PES-01, 0.39% BAC-01.

1.3-1 Solid 1-2-1 was dissolved in MeOH (85 mL), then ca. 40 mL MeOH were distilled off. After a short time, the solid started to precipitate. The suspension was cooled down to RT, a solid was filtered of and washed with acetonitrile (3×10 mL). Solid 1.3-1, 1.43 g (75.26%) was obtained; UPLC: 5.28% RRT(0.95), 92.65% PES-01, 0.21% BAC-01.

1.4-1 Solid 1.3-1 (1.2 g) was dissolved in the boiling MeOH (40 mL) and allowed to cool down. The precipitated solid was filtered off, washed with cold MeOH (2×5 mL), and dried. Solid 1.4-1, 750 mg (62.42%) was obtained; UPLC: 5.07% RRT(0.95), 93.20% PES-01, 0.07% BAC-01.

The results of product purity assays after subsequent steps of crystallization are set forth in the Table 1. Crystallization in MeOH, even 4-fold, does not allow for purification of EC-05.T to a purity higher than 93%. The main impurity is a compound of RRT(0.95).

Example 15

The Process for Purification of EC-05.T by Crystallization in Various Solvent Systems Many attempts of crystallization have been performed in the aim of purification of protoescigenin from the impurities present in EC-05.T mixture. The results were collected in the Tables 2 and 3, wherein RRT, i.e., the relative retention time of the analyzed peak, was determined by the formula:

$$RRT = \frac{RT_{analyzed\ peak}}{RT_{PES-01}},$$

where RT is the recorded retention time.

There are two peaks within RRT=1.07-1.10 for which no good resolution was achieved, so they were treated as the sum of impurities (1.09). Minor impurities were not represented in the tables.

A. Removing of Impurities in the Mixtures of Solvents Selected from Among the Group B ("Non-Polar" Impurities)

Series 2.0 (Table 2)

A mixture of sapogenins (UPLC: 94.12% PES-01, 1.77% BAC-01), 0.5 g, was suspended in acetone and heated to boiling temperature for 5 h, and after then heating was stopped and the suspension was allowed overnight to cool down. The solid was filtered off, washed with acetone, and dried overnight in the drier at 40° C. White precipitate 2.2-5, 0.12 g (25.3%) was obtained, UPLC: 94.70% PES-01, 0.21% BAC-01.

Series 5.0 (Table 2)

5-34. The mixture of sapogenins

Internal Experiment ID: 220.176/F (UPLC: 87.16% PES-01, 5.29% BAC-01), 0.5 g, was dissolved at the boiling temperature in EtOH (3.8 mL). Then, while maintaining the boiling temperature, hexane fraction was added dropwise (16 mL). Heating was turned off and the mixture was allowed to cool down. After several minutes, a solid precipitated out from the solution. The mixture was left overnight. The solid was filtered off, washed with hexane, and dried. A white solid 5-34, 0.36 g (72.8%) was obtained; UPLC: 92.78% PES-01, 0.98% PES-01.

5-39. The mixture of sapogenins from Internal Experiment ID: 220.174/A (UPLC: 87.16% PES-01, 5.29% BAC-01), 0.5 g, was dissolved in boiling i-PrOH (5 mL). Then, while maintaining the boiling temperature, cyclohexane (37 mL) was added dropwise. Heating was turned off and the mixture was allowed to cool down. After several minutes, a solid precipitated out from the solution. The mixture was left overnight. The solid was filtered off, washed with i-PrOH/cyclohexane (5:40), and dried. A white solid 5-39, 0.39 g (77.6%) was obtained; UPLC: 91.06% PES-01, 1.17% BAC-01.

Conclusion

The impurities of RRT≥1.47 are removed in individual $C_1$-$C_3$ alcohols and mixtures thereof, as well as in the mixtures of $C_1$-$C_3$ alcohols with acetonitrile, ethers and hydrocarbons. The content of impurities after single crystallization decreases below a detection level. BAC-01 (RRT=1.14) is purified in all examined solvent mixtures, preferably in alcohol with an admixture of a hydrocarbon or acetonitrile.

The impurity of RRT=1.09 is preferably removed in the mixtures of alcohol and hydrocarbons or acetonitrile and by maceration with acetone.

The impurity of RRT=1.06 is not removable in practice in the solvent systems tested herein (the assays of purity change are within the error of measurement).

The impurity of RRT=0.95 is not removable in the systems tested herein.

B. Removing of Impurities in the Mixtures of Solvents Selected from Among the Group a ("Polar" Impurities)

In Table 3, the examples of removal of the polar impurities, RRT=0.95 and 1.06, as well as an intermediate of RRT=1.09, are set forth.

Series 3.1 (Table 3)

3.1. The mixture of sapogenins from the Internal Experiment ID: 220.107 and 220.136/F, EC-05.T (5.8 g; UPLC 75.8% PES-01, 5.07% BAC-01, 10.98% impurities of RRT 2.17), was dissolved in a boiling mixture consisting of MeOH (155 mL) and acetonitrile (100 mL) and was allowed to cool down to RT. The precipitated solid was filtered off, washed with acetonitrile (2×12 mL), and dried in a vacuum drier at 40° C. The solid 3.1, 3.52 g (60.5%), UPLC: 3.09% RRT (0.95), 78.72% PES-01, 1.36% BAC 01, 8.50% RRT(2.17), was obtained.

3.2-6. The obtained solid 3.1 (0.50 g) was dissolved at 90-100° C. in n-PrOH and water was added (10 mL). The solid precipitated out. After cooling down to RT, the solid was filtered off, washed with n-PrOH/water and dried in a vacuum drier at 40° C. The solid 3.2-6, 0.30 g (60.5%), UPLC: 96.89% PES-01, 1.85% BAC-01, was obtained.

Series 5.0 (Table 3)

5-15. The mixture of sapogenins EC-05.T from the Internal Experiment ID: 220.152/Q, UPLC: RRT(0.95)—3.03%, PES-01—87.16%, BAC-01—5.29%), 0.5 g, was dissolved in propionic acid (10 mL) at 90° C. Then, water was added dropwise to (7.5 mL) and a solid started to precipitate. An additional amount of water was added (2.5 mL portions, 10 mL in total). Heating was turned off and the mixture was allowed to cool down. The solid was filtered off, washed with water, and dried. A white solid 5-15, 0.32 g (64.2%), UPLC: 0.40% RRT(0.95), 90.64% PES-01, 7.26% BAC-01, was obtained.

5-19. The mixture of sapogenins EC-05.T obtained from the Internal Experiment ID: 220.154/P, UPLC: RRT(0.95)—3.03%, PES-01—87.16%, BAC-01—5.29%), 0.5 g, was dissolved in N-methylpyrrolidone NMP (10 mL) at ca. 90° C. Water was added (6 mL), and the solution became turbid. Heating was turned off. After several minutes a precipitate became visible. The suspension was allowed overnight to cool down. The solid was filtered off, washed with water and dried. A white solid 5-19, 0.34 g (67.8%), UPLC: 0.29% RRT(0.95), 91.36% PES-01, 6.87% BAC-01, was obtained.

5-28. The mixture of sapogenins EC-05.T obtained from the Internal Experiment ID: 220.156/C, UPLC: RRT(0.95)—3.03%, PES-01—87.16%, BAC-01—5.29%), 0.5 g, was dissolved in the mixture consisting of MeOH (10 mL) and MTBE (8 mL) under reflux. Water was added (4 mL), and a solid precipitated out. An additional amount of water was added (1 mL). Heating was turned off and the mixture was left overnight to cool down. The solid was filtered off, washed with water and acetonitrile, and dried. A white solid 5-28, 0.30 g (60.8%), UPLC: 0.73% RRT(0.95), 89.79% PES-01, 7.76% BAC-01, was obtained.

Conclusion

The impurity of RRT=0.95 is removed well in all tested solvent systems. The impurity of RRT=1.06 is removed by crystallization in ethanol, propan-2-ol, propionic acid, higher amides and MeOH/ether solvent system, preferably in propan-2-ol/water. The impurity of RRT=1.09 is removed by crystallization in ethanol, propan-2-ol, acetic acid, N-methylpyrrolidone and methanol/ether solvent system, preferably in propan-2-ol/water. In the tested systems, non-polar impurities of RRT≥1.4 are removed as well. However, BAC-01

(RRT=1.14) is not removed. In some samples after acid solvents treatment, an impurity of RRT=1.19 is generated in small amounts.

Example 16

Multi-step Crystallization
Series 6.0 (Table 4)

6-1. A mixture of sapogenins EC-05.T (10.0 g; UPLC: 78.94% PES-01, 12.43% BAC-01), was dissolved in i-PrOH (340 mL) at boiling temperature. The mixture was cooled down to 50° C. and undissolved brown solid was filtered off. The solid was washed with i-PrOH (55 mL), and heated to boiling. Water (330 mL) was added dropwise under reflux. A solid started to precipitate. The mixture was left overnight to cool down to RT. The obtained solid was filtered off, washed with water, and dried overnight in a vacuum drier at 40° C. White solid 6-1, 6.49 g, (64.90%), was obtained.

6-2. The solid 6-1 (6.39 g) was dissolved in i-PrOH (65 mL) and was heated to 60° C. (i-PrOH/cyklohexane aseotrope b.p.). Cyclohexane (CyH) (250 mL) was added dropwise and a solid precipitated out. The mixture was left overnight to cool down to RT. The precipitated solid was filtered off, washed with iPrOH/CyH (1:3; 80 mL) and dried in a vacuum drier. White solid 6-2, 2.458 g (69.5%), was obtained.

6-3. The solid 6-2 (4.50 g) was dissolved in i-PrOH (75 mL), and heated to 60° C. Cyclohexane (400 mL) was added. Heating was removed and the mixture was left overnight to cool down. The solid was filtered off, washed briefly with i-PrOH-cyclohexane mixture (1:4, 2×25 mL), and dried overnight in a laboratory drier at 40° C. White solid 6-3 was obtained, 3.78 g (83.9%), was obtained.

The purity of the products after the subsequent crystallization steps are set forth in Table 4.

The end product obtained by the crystallization in the solvent system i-PrOH-cyclohexane was identified by XRPD, IR (KBr), DSC and TGA methods to be protoescigenin monohydrate (crystalline form III).

The chemical structure of the obtained compound was confirmed by $^1$H NMR and $^{13}$C NMR to correspond to:

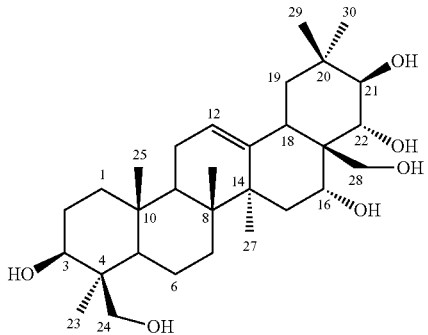

$^1$H NMR (DMSO-d$_6$), δ (ppm): 5.19 (1H, m, H12), 4.96 (1H, d, J=4.8 Hz, C3-OH), 4.43 (1H, dd, J=4.4 and 5.8 Hz, C28-OH), 4.22 (1H, d, J=4.4 Hz, C16-OH), 4.06 (1H, dd, J=3.0 and 7.5 Hz, C24-OH), 4.03 (1H, m, H16), 3.97 (1H, d, J=4.2 Hz, C21-OH), 3.82 (1H, m, H24), 3.81 (1H, d, J=4.9 Hz, C22-OH), 3.79 (1H, dd, J=4.3 and 9.6 Hz, H21), 3.60 (1H, dd, J=5.0 and 9.6 Hz, H22), 3.27 (1H, dd, J=7.6 and 11.0 Hz, H24), 3.18 (1H, m, H3), 3.15 (1H, dd, J=6.0 and 10.2 Hz, H28), 2.99 (1H, dd, J=4.3 and 10.2 Hz, H28), 2.35 (1H, m, H19), 2.27 (1H, dd, J=4.2 and 14.2 Hz, H18), 1.80 (2H, m, H11), 1.62-1.59 (2H, m, H15 and H2), 1.56-1.50 (4H, m, H6, H2, H1 and H9), 1.41 (1H, dd, J=3.9 and 12.7 Hz, H7), 1.37 (1H, dd, J=2.4 and 12.5 Hz, H6), 1.34 (3H, s, C14-CH$_3$ (27)), 1.25 (1H, m, H7), 1.19 (1H, dd, J=2.3 and 14.8 Hz, H15), 1.08 (3H, s, C4-CH$_3$(C23)), 0.94-0.90 (2H, m, H19 and H1), 0.87 (3H, s, C10-CH$_3$(C25)), 0.84 (3H, s, C20-CH$_3$(C29)), 0.81 (3H, s, C8-CH$_3$(C26)), 0.80 (3H, s, C20-CH$_3$(C30)), 0.75 (1H, dd, J=1.8 and 12.0 Hz, H5).

$^{13}$C NMR (DMSO-d$_6$), δ (ppm): 143.1 (C13), 121.8 (C12), 78.6 (C3), 76.8 (C21), 74.0 (C22), 66.6 (C16), 65.2 (C28), 63.0 (C24), 55.4 (C5), 47.2 (C19), 46.2 (C9), 46.0 (C17), 42.1 (C4), 40.9 (C14), 39.5 (C18), 39.2 (C8), 38.2 (C1), 36.3 (C10), 35.3 (C20), 33.2 (C15), 32.8 (C7), 30.0 (CH$_3$ 29), 27.2 (C2), 26.7 (CH$_3$ 27), 23.2 (C11), 22.9 (CH$_3$ 23), 18.8 (CH$_3$ 30), 18.6 (C6), 16.3 (CH$_3$ 26), 15.7 (CH$_3$ 25).

This invention is not to be limited to the specific embodiments disclosed herein and modifications for various applications and other embodiments are intended to be included within the scope of the appended claims. While this invention has been described in connection with particular examples thereof, the true scope of the invention should not be so limited since other modifications will become apparent to the skilled practitioner upon a study of the drawings, specification, and following claims.

All publications and patent applications mentioned in this specification are indicative of the level of skill of those skilled in the art to which this invention pertains. All publications and patent applications mentioned in this specification are herein incorporated by reference to the same extent as if each individual publication or patent application mentioned in this specification was specifically and individually indicated to be incorporated by reference.

The invention claimed is:

1. A process for the preparation of protoescigenin from escin isolated from the horse chestnut *Aesculus hippocastanum*, the process comprising:
   a) a two-step hydrolysis of escin, consecutively under acidic and basic conditions, resulting in obtaining a crude mixture of sapogenins,
   b) a process of enrichment of protoescigenin from the crude mixture of sapogenins, comprising:
      b-i) dissolving the crude mixture of sapogenins in a three-component mixture of solvents to obtain a clear mono- or bi-layer solution, said three-component mixture of solvents comprising:
         a C$_1$-C$_3$ aliphatic alcohol as component 1,
         water as component 2, and
         an aliphatic or cyclic ether as component 3,
      b-ii) addition of water to the clear mono- or bi-layer solution obtained in b-i), until a precipitation of a solid occurs,
   c) isolation of the solid obtained in b-ii),
   d) purification of the solid obtained in c), and
   e) isolation of protoescigenin.

2. The process of claim 1, wherein the hydrolysis is carried out under acidic and basic conditions without isolation of intermediate products from the reaction mixture.

3. The process of claim 1, wherein the steps a) and b) are carried out without isolation of the crude mixture of sapogenins from the reaction mixture.

4. The process of claim 1, wherein component 1 is selected from the group consisting of methanol and propan-2-ol.

5. The process of claim 1, wherein component 3 is selected from the group consisting of tert-butylmethyl ether, diisopropyl ether, and tetrahydrofuran.

6. The process of claim 5, wherein component 3 is tert-butylmethyl ether.

7. The process of claim 1, wherein the three-component mixture of solvents consists of 15-85% (v/v) of methanol, 15-45% (v/v) of water, and the remainder of the three-component mixture being tert-butylmethyl ether.

8. The process of claim 1, wherein the crude mixture of sapogenins obtained in a) is in a form of a suspension, a solution, or an aqueous paste.

9. The process of claim 1, wherein the solid isolated in c) contains more than 70% of protoescigenin as determined by HPLC analysis.

10. The process of claim 1, wherein the purification in d) comprises:
    at least one crystallization process in a mixture of water and a solvent selected from the group consisting of a $C_1$-$C_3$ alcohol; a mixture of a $C_1$-$C_3$ alcohol and an ether; an organic acid; an amide; and dimethylsulfoxide; and
    at least one crystallization process in $C_1$-$C_3$ alcohols; or in a mixture of a $C_1$-$C_3$ alcohol and acetonitrile, an ether, or a saturated hydrocarbon.

11. The process of claim 10, wherein said $C_1$-$C_3$ alcohol is selected from the group consisting of methanol, ethanol, propan-1-ol, and propan-2-ol, said organic acid is selected from the group consisting of acetic acid and propionic acid, and said amide is selected from the group consisting of dimethylformamide, dimethylacetamide, and N-methylpyrrolidone.

12. The process of claim 1, wherein in d), the solid is subject to one crystallization process in a mixture of propan-2-ol and water, and at least one crystallization process in a mixture of propan-2-ol cyclohexane.

13. A process for the isolation of protoescigenin having a purity higher than 98% from a mixture of sapogenins, containing approximately 40-60% of protoescigenin, barringtogenol C, escigenin, and barringtogenol D, as the main impurities, said process comprising:
    i) dissolving the mixture of sapogenins in a three-component mixture of solvents until clear, mono- or bi-layer solution is formed, wherein said three-component mixture of solvents comprises:
        a $C_1$-$C_3$ aliphatic alcohol as component 1,
        water as component 2, and
        an aliphatic or cyclic ether as component 3,
    ii) addition of water to the solution obtained in i), until a precipitation of a solid occurs,
    iii) isolation of the solid precipitated in ii), containing approximately 70-90% of protoescigenin,
    iv) purification of the solid isolated in iii) by a crystallization process, and
    v) isolation of protoescigenin.

14. The process of claim 13, wherein component 1 is selected from the group consisting of methanol and propan-2-ol.

15. The process of claim 13, wherein component 3 is selected from the group consisting of tert-butylmethyl ether, diisopropyl ether, and tetrahydrofuran.

16. Process according to The process of claim 15, wherein component 3 is tert-butylmethyl ether.

17. The process of claim 13, wherein components of the three-component mixture of solvents are methanol, water, and tert-butylmethyl ether.

18. The process of claim 13, wherein the purification in (iv) comprises:
    at least one crystallization step in a mixture of water and a solvent selected from the group consisting of a $C_1$-$C_3$ alcohol; a mixture of a $C_1$-$C_3$ alcohol and an ether; an organic acid; an amide; and dimethylsulfoxide, and
    at least one crystallization step in $C_1$-$C_3$ alcohols; or in a mixture of a $C_1$-$C_3$ alcohol and acetonitrile, an ether, or a saturated hydrocarbon.

19. The process of claim 18, wherein said $C_1$-$C_3$ alcohol is selected from the group consisting of methanol, ethanol, propan-1-ol, and propan-2-ol; said organic acid is selected from the group consisting of acetic acid and propionic acid; and said amide is selected from the group consisting of dimethylformamide, dimethylacetamide, and N-methylpyrrolidone.

20. The process of claim 18, wherein the solid obtained in iii) is purified by one crystallization step in a mixture of a $C_1$-$C_3$ alcohol and water, and at least one crystallization step in a mixture of a $C_1$-$C_3$ alcohol and a saturated hydrocarbon.

21. The process of claim 20, wherein the solid obtained in iii) is purified by one crystallization step in a mixture of a $C_1$-$C_3$ alcohol and water, and at least one crystallization step in a mixture of propan-2-ol and cyclohexane.

22. The process of claim 18, wherein protoescigenin is isolated in a form of monohydrate having a purity higher than 98% as determine by UPLC analysis.

23. The process of claim 9, wherein the solid isolated in c) comprises 75-90% of protoescigenin as determined by HPLC analysis.

* * * * *

UNITED STATES PATENT AND TRADEMARK OFFICE
CERTIFICATE OF CORRECTION

PATENT NO. : 9,073,813 B2
APPLICATION NO. : 13/733855
DATED : July 7, 2015
INVENTOR(S) : Mariusz Gruza et al.

It is certified that error appears in the above-identified patent and that said Letters Patent is hereby corrected as shown below:

In the Claims:

In Column 23, Line 29, in Claim 12, delete "propan-2-ol cyclohexane" and insert -- propan-2-ol and cyclohexane --, therefor;

In Column 24, Line 10, in Claim 16, delete "Process according to The process of claim" and insert -- The process of claim --, therefor.

Signed and Sealed this
Twelfth Day of April, 2016

Michelle K. Lee
*Director of the United States Patent and Trademark Office*